United States Patent
Carstens et al.

(10) Patent No.: US 6,582,411 B1
(45) Date of Patent: Jun. 24, 2003

(54) HIGHLY EFFICIENT ABSORBENT ARTICLE FOR USE WITH MENSTRUAL PANT

(75) Inventors: Jerry Edward Carstens, West Chester, OH (US); Letha Margie Hines, Cincinnati, OH (US); Nicholas Albert Ahr, Cincinnati, OH (US); Diane Dunn Farris, West Chester, OH (US); Nona Jane Redwine, Mason, OH (US); Deborah Catherine Schmitz, West Chester, OH (US); Cynthia Lee Alvis, Fairfield, OH (US); John Richard Noel, Cincinnati, OH (US); Ronald Ray McFall, West Chester, OH (US); Thomas Ward Osborn, III, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/554,488
(22) PCT Filed: Nov. 9, 1998
(86) PCT No.: PCT/US98/23861
§ 371 (c)(1),
(2), (4) Date: May 15, 2000
(87) PCT Pub. No.: WO99/25290
PCT Pub. Date: May 27, 1999

Related U.S. Application Data
(60) Provisional application No. 60/065,294, filed on Nov. 13, 1997.

(51) Int. Cl.[7] .................................................. A61F 13/15
(52) U.S. Cl. .......................... 604/385.01; 604/385.23; 604/378; 604/385.101; 604/385.29; 604/385.3; 604/358; 604/369; 604/385.01; 604/385.31
(58) Field of Search ................................ 604/358, 369, 604/385.01, 385.29, 385.31, 378

(56) References Cited

U.S. PATENT DOCUMENTS

| | | | | |
|---|---|---|---|---|
| 5,300,055 A | * | 4/1994 | Buell | 604/385.23 |
| 5,383,868 A | | 1/1995 | Hyun | |
| 5,647,862 A | * | 7/1997 | Osborn et al. | 604/368 |
| 5,672,165 A | | 9/1997 | Belecky et al. | |

FOREIGN PATENT DOCUMENTS

| | | | |
|---|---|---|---|
| EP | 0 302 523 A2 | 2/1989 | |
| EP | 0 597 498 A1 | 5/1994 | |
| EP | 0 685 212 A2 | 12/1995 | |
| GB | 2 282 054 A | 3/1995 | |
| WO | WO 93/21879 | * 11/1993 | A61F/13/15 |
| WO | WO 96/20670 | * 7/1996 | A61F/13/15 |
| WO | WO 98/33463 | 8/1998 | |

* cited by examiner

*Primary Examiner*—John J. Calvert
*Assistant Examiner*—Angela J Grayson
(74) *Attorney, Agent, or Firm*—Matthew P. Fitzpatrick; Ingrid W. Hickman; Kevin C. Johnson

(57) ABSTRACT

Highly efficient absorbent articles for wearing by a human female such as sanitary napkins, panty liners, and adult incontinence pads. In use, the absorbent articles preferably maintain contact with and cover at least a portion of the inside surfaces of the wearer's labia, the exterior surfaces of the wearer's labia, and the supporting garment. The absorbent articles are highly flexible, having flexure resistance of less than or equal to about 100 grams. The absorbent articles may be flat or cup-shaped.

28 Claims, 11 Drawing Sheets

HIGHLY EFFICIENT ABSORBENT ARTICLE FOR USE WITH MENSTRUAL PANT

This application claims the benefit of provisional application No. 60/065,294 filed Nov. 13, 1997.

FIELD OF THE INVENTION

The present invention relates to absorbent articles such as sanitary napkins, panty liners, incontinence pads, and the like. More particularly, the present invention relates to a highly efficient absorbent article for use with a supporting garment, such as a menstrual pant (or panty).

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineum. Sanitary napkins of a wide variety of shapes and dimensions are currently used by women for the collection of menses and other bodily discharges.

In the past, a number of efforts have been directed at providing sanitary napkins that maintain contact with the wearer's body. One attempt to provide such body contact is disclosed in U.S. Pat. No. 2,747,575 issued May 29, 1956 to Mercer. The Mercer patent discloses a catamenial bandage having a longitudinal hump which bulges towards and may contact the body of the wearer. The catamenial bandage described in the Mercer patent suffers from several disadvantages, however. For instance, the size and shape of the absorbent pad and hump in the Mercer bandage appear to limit the conditions under which the bandage is able to maintain contact with (and conform to) the body of the wearer.

U.S. Pat. No. 4,425,130 issued to DesMarais on Jan. 10, 1984, discloses a compound sanitary napkin that comprises a primary menstrual pad and a panty protector joined to one another at their corresponding ends in such a manner that the two constituents are free to move relative to one another along essentially their entire common length. The primary menstrual pad is intended to absorb the bulk of the bodily fluids discharged by the user, while the panty protector is intended to protect the user's garments from soiling. In use, the relative freedom of movement between the primary menstrual pad and the panty protector serves to maintain the primary menstrual pad adjacent the user's crotch region while the panty protector remains associated with the user's undergarment.

It is also desirable that sanitary napkins, not only maintain contact with, but conform as closely as possible to the wearer's body. Such a body-conforming capability increases the effectiveness of the sanitary napkin by reducing the possibility that menses will travel around the perimeter of the sanitary napkin and leak. There have been a number of recent efforts to provide sanitary napkins and other absorbent articles with improved body-conforming characteristics. For example, U.S. Pat. No. 4,950,264 issued to Osborn on Aug. 21, 1990, is directed to a thin, flexible sanitary napkin that is capable of handling medium to high menstrual flows. The sanitary napkin in the Osborn patent is described as being highly flexible and conforming very well to the various shapes of the female urogenital region. The Osborn patent discloses a sanitary napkin having a flexure resistance of less than about 130 grams; a test capacity of at least about 8 grams (per a 66.5 square centimeter section); and a total capacity of at least about 20 grams. The sanitary napkin may have a caliper of 2 mm, or less. The Osborn sanitary napkin is described as being worn in the wearer's underwear, and is preferably scaled to the width of the crotch of the wearer's underwear.

In addition, PCT International Patent Application Publication No. WO 94/16658, entitled "Generally Thin, Flexible Sanitary Napkin With Central Absorbent Hump", published in the name of Osborn on Aug. 4, 1994, discloses a generally thin, flexible sanitary napkin which has a central absorbent hump, and is capable of handling medium to high menstrual flows. The hump is particularly useful in fitting into the space between the wearer's labia to more readily intercept menses and other bodily discharges when they leave the wearer's body. The search, however, has continued for improved sanitary napkins, particularly sanitary napkins that will achieve even better fit.

For example, current sanitary napkins are typically worn in a loose-fitting undergarment. Such sanitary napkins are necessarily designed to be large enough so that in the event of any shifting of the sanitary napkins from their position under the vaginal introitus, they will still be able to intercept the wearer's bodily discharges. Thus, a need exists for an absorbent article that fits closely, and comfortably against the wearer's body which is not required to be designed to compensate for poorly-fitting undergarments.

It has been theorized by the inventors that if an absorbent article with sufficiently high capacity is held closely but comfortably against the wearer's pudendal region, and in particular, covers the vaginal introitus, the surfaces of the labia majora, and perineum, during the entire period throughout which the absorbent article is worn, then an absorbent article can be provided which is of a greatly reduced size in comparison to current sanitary napkins. Such an absorbent article need only be large enough to cover these regions of the wearer's body, rather than being sized to accommodate shifting of the product with respect to the introitus.

SUMMARY OF THE INVENTION

The present invention is directed to highly efficient absorbent articles for wearing by a human female such as sanitary napkins, panty liners, and adult incontinence pads ("absorbent pads") for use with a specially designed supporting garment (or undergarment), such as a menstrual pant (or panty).

The absorbent article of the present invention preferably maintains contact with and covers the inside surfaces of the wearer's labia, the exterior surfaces of the wearer's labia, and covers the menstrual panty. Coverage of all three of these surfaces provides the absorbent article with the greatest opportunity to provide superior leakage protection and to maintain the wearer's body in a clean condition, free of menses. The absorbent article is preferably worn with a menstrual panty that comfortably fits against and conforms to the inside and outside surfaces of the wearer's labia majora. This conforming fit is present regardless of whether the wearer's legs are apart, or together. The menstrual panty preferably maintains a modified cusp-shaped cross-sectional configuration in this area throughout a range of body motions. The absorbent article preferably does not alter or override the tendency of the menstrual panty to achieve this fit. The absorbent article preferably flexes under the forces exerted by the menstrual panty so that it assumes a similar (and preferably the same modified cusp shape) in this region as the menstrual panty.

The absorbent article and menstrual panty preferably function in a manner that can be thought of as being analogous to covering a cut with a bandage. Body fluids are captured at or near their source by using close body contact and comfortable forces to hold the absorbent article in place at the source of bodily fluids. This can be contrasted with using overly-sized sanitary napkin in a loose-fitting pair of panties, which function in a manner that can be analogized to the use of a drop cloth beneath the source of bodily fluids. The absorbent article is preferably sufficiently small that it only covers the wearer's pudendal region and immediately adjacent regions, and in particular, covers the vaginal introitus and the surfaces of the labia majora. The absorbent article may also cover the wearer's perineum. The absorbent article preferably does not extend forward beyond the wearer's mons pubis. The absorbent article preferably does not extend rearward to contact the wearer's anus to avoid sensitive nerve endings therein. This provides a more comfortable, and less noticeable absorbent article since it occludes less of the crotch region of the wearer's body and allows air to circulate around the same. The absorbent article preferably cups the labia from front to back.

The absorbent article also preferably does not cover areas of the wearer's body that undergo substantially degrees of movement (that is, the absorbent article will only be placed adjacent to "low motion zones" of the wearer's body). In particular, it is desirable that the edges of the absorbent article will not be contacted by the inside surfaces of the wearer's thighs when the wearer walks, or otherwise moves about. This overcomes a drawback of conventionally-sized sanitary napkins and pantiliners, which being comparatively stiff relative to the absorbent article of the present invention, will transfer forces applied to the edges thereof to other portions of the sanitary napkin or pantiliner, causing the same to bend or crumple, and/or shift from the desired position under the wearer's vaginal introitus.

In several embodiments, the absorbent article of the present invention comprises a liquid pervious topsheet, a liquid resistant, or liquid impervious backsheet joined to the topsheet, and an absorbent core positioned between the topsheet and the backsheet. In one embodiment, the absorbent article has a cup-shaped configuration. In other embodiments, the absorbent article can be generally flat prior to use. The absorbent article, as discussed above, is substantially smaller than conventional sanitary napkins. For example, if cup-shaped, the absorbent article may have an overall length when measured in its curved configuration of less than or equal to about 6 or 7 inches (about 15 cm to about 18 cm), or even less than or equal to about 5 inches (about 12.7 cm), and a width of less than or equal to about 3 inches (about 7.6 cm). In one preferred embodiment the absorbent article measures about 6 inches (about 15 cm) by about 3 inches (about 7.6 cm). The absorbent article of the present invention preferably has a surface area measured in flat condition that can be less than or equal to about any of the following: about 20 in$^2$ (about 130 cm$^2$); about 18 in$^2$ (116 cm$^2$); about 15 in$^2$ (about 97 cm$^2$ (or 100 cm$^2$)); about 12.5 in$^2$ (about 80 cm$^2$); or about 10 in$^2$ (about 65 cm$^2$).

The absorbent article is preferably highly flexible, and preferably has a flexure resistance of less than or equal to about 100 grams, more preferably less than or equal to about 70 grams, and most preferably between about 30 and about 50 grams. The absorbent article preferably has a total capacity of greater than or equal to about 20 grams of liquid, more preferably greater than or equal to about 25 grams of liquid. The absorbent article preferably has a ratio of total capacity to surface area of greater than or equal to about 2 g/in$^2$ (about 0.3 g/cm$^2$), more preferably greater than or equal to about 2.5 (g/in$^2$) (about 0.4 g/cm$^2$).

In one particularly preferred embodiment, the topsheet of the absorbent article comprises a high loft fibrous material. The absorbent article with the high loft fibrous material is preferably comprised of fine polymeric fibers that provide a plurality of filamentary members for contacting the wearer's body. The high loft fibrous topsheet material serves several functions. It allows the absorbent article to achieve a "macro" fit that is capable of fitting virtually all women, and a "micro" fit that adjusts to the particular body contours of individual women. The high loft topsheet also tends to break the flow of menses along the wearer's body, and intercepts menses flowing along the wearer's body, and allows such bodily exudates to be acquired into the absorbent core. The absorbent core can comprise a variety of different high efficiency absorbent cores. In one preferred embodiment, the absorbent core comprises a highly porous HIPE polymeric foam that is preferably either slit, in the form of strands, particles, or a plurality of upright, spaced apart columns. The term "HIPE polymeric foams" refers to hydrophilic, flexible open-celled foam structures which are preferably prepared by polymerizing high internal phase (HIPE) water-in-oil emulsions. The backsheet can comprise a conventional liquid impervious film, or a breathable material.

The absorbent article may be provided with other optional features. In some embodiments, the absorbent article may be provided with elastics, preferably in the form of an elastomeric film/nonwoven laminate along the longitudinal edges thereof for forming the absorbent article in a cup-shaped configuration, in a manner that is comfortable for the wearer. The absorbent article may have a fastener for fastening the absorbent article to the specially designed supporting garment. In a preferred embodiment, the absorbent article has a plurality of fine hair-like projections on the garment-facing surface thereof which engage with and adhere to a specially designed knit supporting garment. In other embodiments, the absorbent article may be provided with a raised portion on its body-facing side. In such a case, the absorbent article may have an absorbent tube on its body-facing side so that it is in the form of a "compound" absorbent article.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Figure 1:
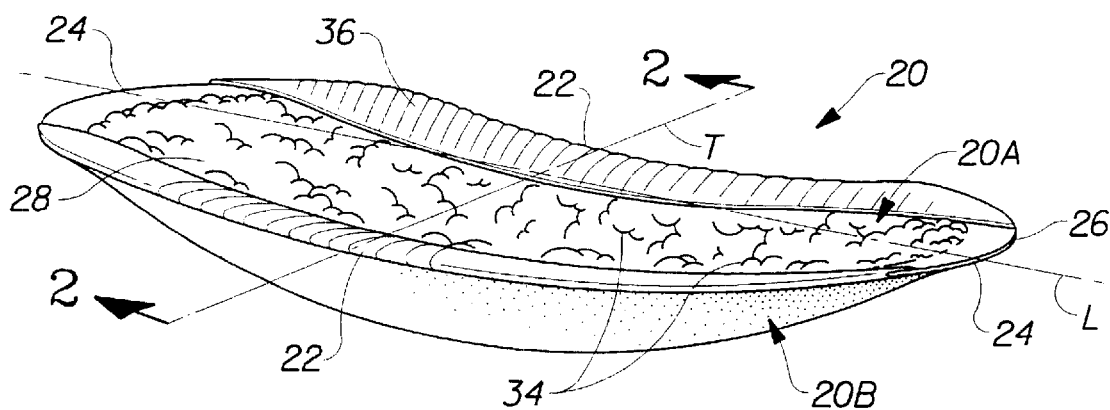
FIG. 1 is a perspective view of one embodiment of an absorbent article of the present invention.

The present invention is directed to absorbent articles for wearing by a human female such as sanitary napkins, panty liners, and adult incontinence pads. The absorbent articles of the present invention are intended for use with a specially-designed supporting garment (or undergarment), such as a menstrual pant (or panty).

1. The Absorbent Article

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinence pads (and other articles worn in the crotch region of a garment).

The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) In the preferred embodiments illustrated in FIGS. 1–3, the absorbent article is a menstrual pad designated 20 that is designed to replace conventional sanitary napkins.

The term "sanitary napkin", as used herein, refers to an article which is worn by females adjacent to the pudendal region that is intended to absorb and contain the various exudates which are discharged from the body (e.g., blood, menses, and urine). Although the present invention is shown in the drawings as a menstrual pad that is intended to replace conventional sanitary napkins, it should be understood that the present invention is not limited to the particular types or configurations of absorbent articles shown in the drawings.

The absorbent article 20 of the present invention has two surfaces, a liquid pervious side, body-contacting surface or "body surface" 20A and a liquid impervious side, garment surface 20B. The absorbent article 20 is shown in FIG. 1 as generally viewed from its body surface 20A. The body surface 20A is intended to be worn adjacent to the wearer's body. The garment surface 20B is intended to be placed adjacent to the supporting garment when the absorbent article 20 is worn.

The absorbent article 20 has two centerlines, a longitudinal centerline L and a transverse centerline T. The term "longitudinal", as used herein, refers to a line, axis or direction in the plane of the absorbent article 20 that is generally aligned with (e.g., approximately parallel to) a vertical plane which bisects a standing wearer into left and right body halves when the absorbent article 20 is worn. The terms "transverse" or "lateral" used herein, are interchangeable, and refer to a line, axis or direction which lies within the plane of the absorbent article 20 that is generally perpendicular to the longitudinal direction.

The absorbent article has two spaced apart longitudinal edges 22, two spaced apart transverse or end edges (or "ends") 24, which together form the periphery 26 of the absorbent article. In the embodiment shown in FIGS. 1–3, the absorbent article 20 has a cup-shaped configuration from front to back and side to side. In other embodiments, the absorbent article 20 may be in a flat configuration.

The absorbent article 20 may also have any suitable plan view configuration. Suitable configurations include, but are not limited to: oval; race-track shaped; shapes which have convexly-inward longitudinal side edges (e.g., hourglass shapes); key-hole shapes which have a wider rounded or oval portion which is preferably worn toward the rear of the wearer's body, preferably for covering at least a portion of the wearer's perineum and a generally rectangular extension therefrom (preferably with rounded edges) which is preferably worn toward the front of the wearer's body for covering at least a portion of the wearer's pudendal region. In the particularly preferred embodiment shown in FIGS. 1–3, the absorbent article has a racetrack-like plan view configuration with straight longitudinal side edges and convexly curved end edges.

The absorbent article is preferably substantially smaller than conventional sanitary napkins. For example, the absorbent article may have an overall length when measured in its curved configuration of less than or equal to about 6 or 7 inches (about 15 cm to 18 cm), or even less than or equal to about 5 inches (about 12.7 cm), and a width of less than or equal to about 3 inches (about 7.6 cm). In one preferred embodiment the absorbent article measures about 6 inches (about 15 cm) by about 3 inches (about 7.6 cm). The absorbent article of the present invention preferably has a surface area measured in flat condition and exclusive of any flaps, wings, or side wrapping elements that can be less than or equal to about any of the following: about 20 in$^2$ (about 130 cm$^2$); about 18 in$^2$ (116 cm$^2$); about 15 in$^2$ (about 97 cm$^2$ (or 100 cm$^2$)); about 12.5 in$^2$ (about 80 cm$^2$); or about 10 in$^2$ (about 65 cm$^2$).

The absorbent article is preferably highly flexible, and preferably has a flexure resistance of less than or equal to about 100 grams, more preferably less than or equal to about 70 grams, and most preferably between about 30 and about 50 grams. This allows the absorbent article to conform very closely to the wearer's body. It also allows the absorbent article to conform to the shape assumed by the crotch region of the specially designed supporting garment. In other words, the absorbent article will bend under the body-contacting forces (described in greater detail below) applied by the supporting garment, and will not "overpower" the second skin fit of the supporting garment. The small size and high flexibility also provides the absorbent article with improved comfort.

The absorbent article 20 is preferably also highly absorbent. The absorbent article preferably has a total capacity of greater than or equal to about 10 grams, more preferably about 20 grams or greater than or equal to about 25 grams of liquid. Total capacity is measured in accordance with the method described in the Test Methods section of this specification. It is particularly desirable that the portion of the absorbent article 20 that is placed adjacent to the wearer's vaginal orifice have the aforementioned capacity, particularly a region which measures 2 inches by 5 inches (5 cm by 13 cm) which would be centered under the vaginal orifice when the absorbent article is worn. To determine the capacity for this 2 inch by 5 inch area, a rectangular area having such dimensions is cut from the portion of the absorbent article to be tested that would be centered under the vaginal orifice. The test is run on this 2×5 portion of the absorbent article in the same manner as the capacity test described in the Test Methods section of this specification. If the absorbent article is smaller than 2 inches by 5 inches in this region, then a sample of the absorbent article which would lie within a 2 inch by 5 inch rectangle is used.

The highly efficient nature of the absorbent article may also be expressed in terms of the ratio of the total capacity of the absorbent article to the surface area of the absorbent article. In some preferred embodiments, the absorbent article preferably has a ratio of total capacity to surface area (the latter being measured in a flat condition) of greater than or equal to about 2 (g/in$^2$) (about 0.30 g/cm$^2$), more preferably greater than or equal to about 2.5 (g/in$^2$) (about 0.39, or about 0.40 g/cm$^2$). By way of comparison, the capacity to surface area ratio of an ALWAYS ULTRA thin sanitary napkin sold by The Procter & Gamble Company of Cincinnati, Ohio is about 1.7 (g/in$^2$) (about 0.26 g/cm$^2$). The absorbent article 20 is highly efficient, having an overall capacity greater than or equal to a current ultra thin sanitary napkin, while being roughly half the size.

Figure 2:
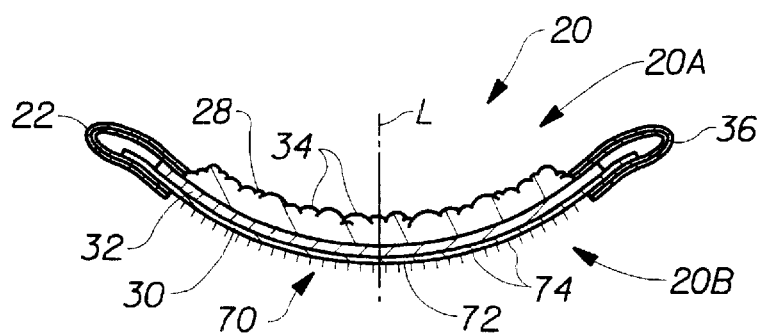
FIG. 2 is a cross-sectional view of the absorbent article shown in FIG. 1, taken along line 2—2.

FIG. 2 shows the individual components of the absorbent article 20 of the present invention. This embodiment of the absorbent article 20 preferably comprises at least three primary components. These include a liquid pervious topsheet 28, a liquid impervious backsheet 30, and an absorbent component, such as absorbent core 32 positioned between the topsheet 28 and the backsheet 30. The liquid pervious topsheet, the liquid impervious backsheet, and the absorbent core can comprise a number of suitable materials, provided that the absorbent article 20 has the overall characteristics described herein.

It should also be understood that the absorbent article 20 of the present invention is not limited to structures which have these three primary components. Embodiments can be provided which only have one or two of these components. For example, the absorbent article 20 need not have a topsheet if the body-facing surface of the absorbent core is suitable for use as a topsheet. A liquid impervious component, such as a liquid impervious backsheet, could be joined to the other side of the absorbent component. Alternatively, the absorbent article 20 can comprise an absorbent component that has a liquid pervious side and a liquid impervious side.

The liquid impervious side can be provided by treating the garment surface of the absorbent component to render it liquid impervious.

The liquid pervious side defines the body-contacting surface of the absorbent article 20. In some preferred embodiments, the liquid pervious side comprises a plurality of elements extending outward from the body-contacting surface of the absorbent article 20. That is, if the body-contacting surface is considered to lie within the X-Y plane in a Cartesian coordinate system, these elements will extend outward from this plane in the Z-direction, though not necessarily perpendicular to this plane. These elements can form any suitable angle with the body-contacting surface of the absorbent article 20. The elements can comprise any suitable type of components, including, but not limited to fibers.

Figure 3:
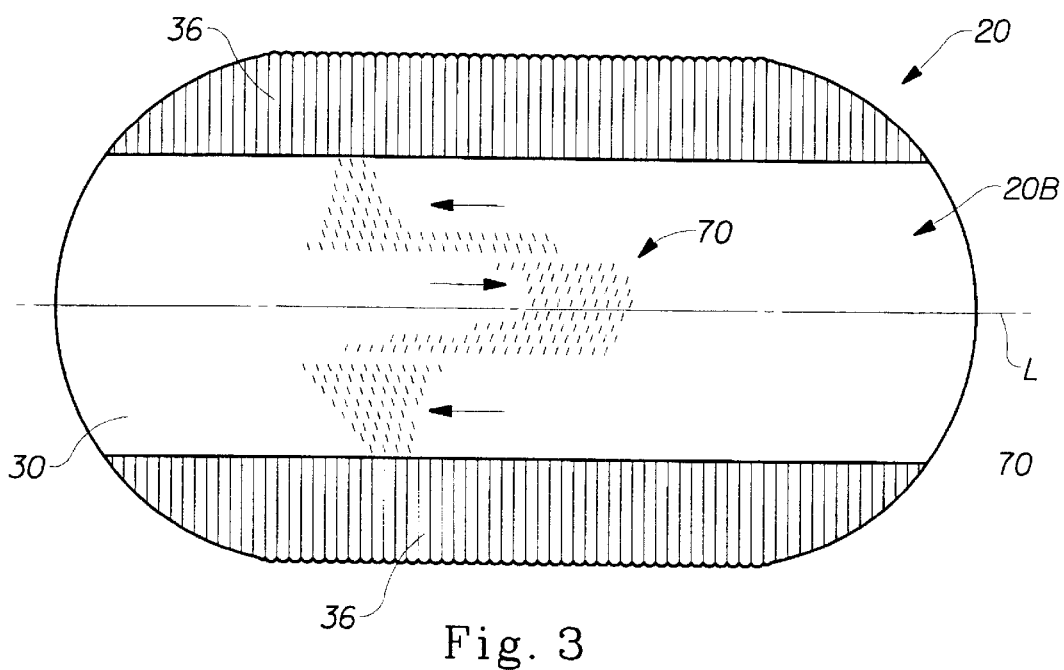
FIG. 3 is a bottom plan view of the absorbent article shown in FIG. 1.

In the embodiment shown in FIGS. 1–3, the liquid pervious topsheet 28 comprises a high loft fibrous material. The term "high loft fibrous material", as used herein, refers to a low density, but relatively high caliper, fibrous material. The high loft fibrous material preferably has a density of less than or equal to about 0.01 g/cm$^3$. The high loft fibrous material preferably has a caliper of greater than or equal to about ⅛ inch (about 3.2 mm), more preferably between about ¼ inch (about 6.4 mm) and at least about ½ inch (about 13 mm). The high loft fibrous material preferably has a basis weight of less than or equal to about 4 or 5 oz./square yard (about 142 grams/m$^2$). These calipers and densities were measured under INDA standard test method IST 720.1-92, which specifies measuring caliper under a pressure of 0.005 psi. (350 Pa).

The high loft fibrous material is preferably comprised of fine polymeric fibers 34, which preferably have a denier per fiber of less than or equal to about 6. The high loft fibrous topsheet material serves several functions. It allows the absorbent article to achieve a "macro" fit that is capable of fitting virtually all women, and a "micro" fit that adjusts to the particular body contours (which may be in the form of rugosities) of individual women. Another advantage of the high loft topsheet is that it is very soft and "cushiony". The high loft topsheet also is advantageous because it has a low coefficient of friction against the wearer's body due to the discrete contact of the individual fibers comprising the same with the wearer's body.

In addition, it is often assumed that leakage of menses from conventional sanitary napkins occurs primarily as a result of the capacity of absorbent articles being exceeded. However, it has been found that a substantial number of soiling accidents occur as a result of menstrual fluid that does not even enter the sanitary napkin. Often these soiling accidents result from menses which flows adjacent to the wearer's body, and which may flow in or close to the wearer's pubic hair. A high degree of "loft" is preferred so that the fibers of the topsheet will get into close contact with the wearer's body and between the wearer's pubic hairs. The high loft topsheet tends to break the flow of menses along the wearer's body, and intercepts menses flowing along the wearer's body, and allows such bodily exudates to be acquired into the absorbent core. Such high loft topsheets provide a capillary structure the effectively competes with the wearer's body for bodily fluids, such as menses, and directs such fluids into the absorbent article. A good indicator of whether an absorbent article has a body-contacting surface with Z-direction oriented elements is whether the elements on the body-contacting surface are capable of penetrating between the wearer's pubic hairs. Conversely, if the elements comprising the body-contacting surface of the absorbent article lie flat against the wearer's pubic hairs, and compress the pubic hairs, this is an indication that the absorbent article does not have a body-contacting surface with Z-direction oriented elements.

In preferred embodiments, the high loft topsheet comprises a thermally bonded carded polyester fibrous nonwoven material having a caliper of about 4 mm and a basis weight of about 1.5 oz./yd$^2$ (about 50 grams/m$^2$). The fibers 34 of this high loft topsheet material are preferably in a random orientation. One particularly preferred material for the high loft topsheet has a caliper of 4.1 mm, and a density of 0.0077 g/cm$^3$, and is obtained as product code #W-4635 from Steams Technical Textile of Cincinnati, Ohio. Another preferred high loft topsheet material has a caliper of 5.8 mm, and a density of 0.0098 g/cm$^3$ (after rebulking), and is obtained as product code r #68317 (rebulked) from Fibertex A/S, Box 8029, Svendborgvej 16, DK-9220 Aalborg Ost, Denmark. If the high loft topsheet material has one side that is relatively flat, and one side that is "fluffy", it is preferred that the flat side be oriented toward the absorbent core.

The fibers of the high loft topsheet material are preferably slightly hydrophobic. Once bodily exudates contact the fibers of the high loft topsheet, they are transported down through the high loft topsheet and penetrate very quickly into the absorbent core. For example, the high loft topsheet may have an acquisition rate of from about 0.27 ml/sec. to about 0.75 ml/sec., while current apertured formed films, such as the DRI-WEAVE topsheet material described below, may have an acquisition rate of about 0.15 ml/sec. The fibers, although thin, lay on top of one another to form a top layer with large openings therein. Menses falls through the large openings between the fibers of the high loft topsheet into the underlying absorbent core. The high loft topsheet material has considerable depth and, as a result, is able to keep the wearer's body relatively dry (or reduce "rewet") by spacing the absorbent core (and liquids held therein) away from the wearer's body.

In other embodiments, the fibers of the high loft topsheet may have a degree of hydrophilicity, or may be treated with a surfactant to provide them with a degree of hydrophilicity. This may allow the fibers to more effectively draw menses away from the wearer's skin.

Figure 4:
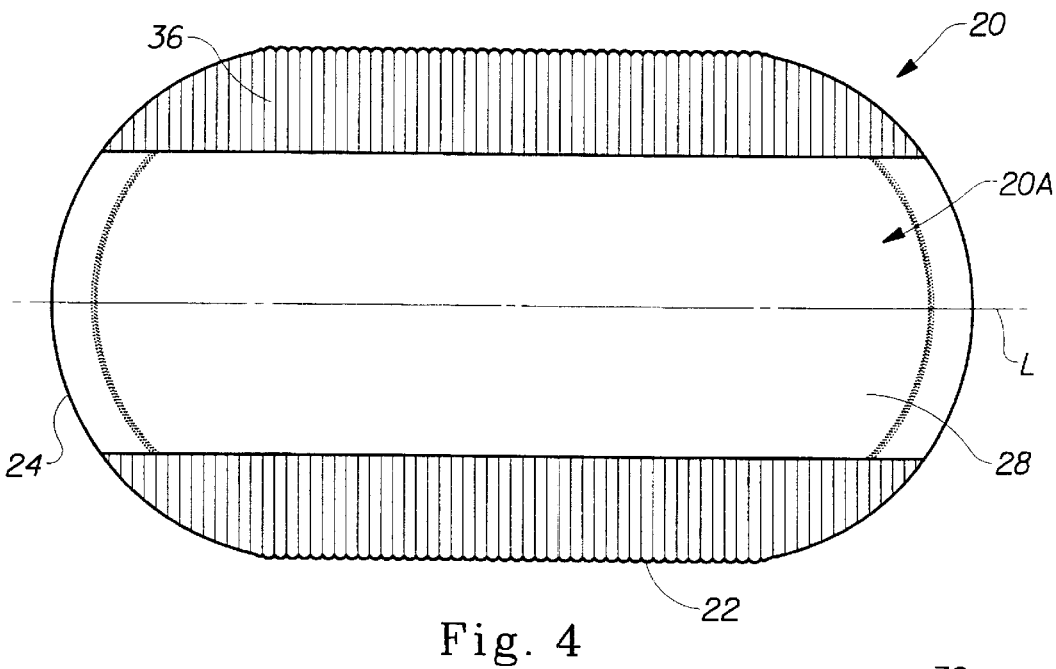
FIG. 4 is a top plan view of an embodiment of the absorbent article of the present invention having another type of topsheet.

In still other embodiments such as the embodiment shown in FIG. 4, the liquid pervious topsheet 28 may comprise an apertured film, such as an apertured formed film. Suitable formed films are described in U.S. Pat. No. 3,929,135, issued to Thompson on Dec. 30, 1975; U.S. Pat. No. 4,324,245, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird, on Apr. 9, 1991. One especially preferred material for the topsheet 28 comprises a formed film described in one or more of the above patents and marketed on sanitary napkins by The Procter & Gamble Company of Cincinnati, Ohio as the "DRI-WEAVE" topsheet. The topsheet 28 preferably has a hydrophilic surfactant incorporated therein during manufacture.

Other preferred apertured films suitable for use as the topsheet 28 are the apertured films made in accordance with U.S. Pat. Nos. 4,609,518 and 4,629,643, the latter entitled "Microapertured Polymeric Web Exhibiting Soft and Silky Tactile Impression", both issued to Curro, et al., on Sep. 2, 1986, and Dec. 16, 1986, respectively, and cloth-like formed films made in accordance with U.S. Pat. No. 4,637,819 entitled "Macroscopically Expanded Three-Dimensional Polymeric Web for Transmitting Both Dynamically Deposited and Statically Contacted Fluids From One Surface to the Other", which issued to Ouellette, et al. on Jan. 20, 1987; and U.S. patent application Ser. No. 08/442,935 entitled "Fluid Transport Webs Exhibiting Surface Energy Gradients" filed in the name of Ouellette, et al. on May 31, 1995 (PCT Publication WO 96/00548, published Jan. 11, 1996).

If such an apertured film topsheet material is used, it can be used as the topsheet 28 per se. Preferably, however, it is used in conjunction with high loft topsheet material wherein the high loft topsheet material overlies such an apertured film. The apertured film, if properly apertured, will provide a reduced tendency for liquids to pass back through and rewet the wearer's skin. Combining both the high loft topsheet material and the cloth-like apertured formed film adds additional thickness to the above-described high loft layer and further spaces the absorbent core and liquids therein from the wearer's body, further contributing to keeping the wearer's body dry.

In another embodiment, the apertured film in the embodiments described above may be replaced by an apertured fibrous web having an apertured portion an a nonapertured portion. The apertured fibrous web has a body surface provided with a plurality of fibrils or "hairs" on the nonapertured portion thereof. Preferably, the apertured fibrous web is wet laid and has a temporary wet strength resin incorporated therein, and the fibrils comprise a water resistant resinous material. In a preferred version of this embodiment, the fibrous web comprises an apertured cellulosic tissue with fibrils printed thereon. The fibrils reduce the surface wetness characteristics of the fibrous tissue by separating the wearer's body from any bodily fluids that may remain on the body side of the fibrous tissue. The printed, wet laid apertured tissue, the method for producing the tissue, and the resin application method are more fully described in U.S. Pat. No. 5,763,044 entitled "Fluid Pervious, Dispersible, and Flushable Webs Having Improved Functional Surface", issued to Ahr, et al.

The absorbent core 32 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles. The absorbent core 32, however, should preferably be adapted so that it has the capacity specified herein. Examples of suitable absorbent materials include comminuted wood pulp which is generally referred to as airfelt; creped cellulose wadding; meltblown polymers including coform; chemically stiffened, modified or cross-linked cellulosic fibers, synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures. Examples of suitable absorbent core materials with sufficient capacity are described below.

In one embodiment, the absorbent core 32 comprises an airlaid web with particulate or fibrous superabsorbent hydrogel-forming polymeric material dispersed therein. The airlaid web can comprise a number of different types of materials. In one version of this embodiment, the absorbent core may comprise a blend of synthetic polymeric fibers, cellulosic fibers, and particulate or fibrous superabsorbent hydrogel-forming polymeric material. In another version of this embodiment, the absorbent core may comprise only synthetic polymeric fibers and fibrous or particulate superabsorbent hydrogel-forming polymeric material. In still another version of this embodiment, the absorbent core may be comprised entirely of cellulosic fibers (such as airfelt) and particulate or fibrous superabsorbent material. However, it is preferred that the absorbent core comprise at least some synthetic material to increase its compression resistance and resiliency.

A suitable fibrous superabsorbent, hydrogel-forming polymeric material is sold as FIBERDRI superabsorbent by Camelot Technologies Ltd. of High River, Canada. The FIBERDRI fibrous superabsorbent material is preferred because it has more capacity than many current particulate superabsorbent materials. For example, it may have a capacity of about 25 grams of liquid per gram of superabsorbent material, whereas current particulate superabsorbent materials may have a capacity of about 20 grams/gram. The FIBERDRI material, thus, provides the advantage that a relatively small amount (for example, about 0.7 grams) of the FIBERDRI material will provide a total amount of capacity for the small sized absorbent core used in the present invention, which is equal to or greater than the total amount of capacity of full-sized sanitary napkins.

In another embodiment, the absorbent core 32 can comprise a laminate of tissue and superabsorbent hydrogel-forming polymeric material. Absorbent cores comprising laminates of tissue and superabsorbent hydrogel-forming polymeric material which can be modified for use herein are described generally in U.S. Pat. Nos. 4,950,264 and 5,009,653, both issued to Osborn.

In one version of such an embodiment, the absorbent core 32 has three longitudinally oriented trisections, a central trisection flanked by two laterally outboard trisections. The absorbent core is formed of a single layer of tissue. The single layer of tissue is folded on itself to provide a two-ply thickness at each of the outboard trisections and a single thickness at the central trisection. The two plies of the outboard trisections are preferably adhered together. Absorbent gelling materials are disposed in each of the outboard trisections. The central trisection may be substantially free of absorbent gelling materials. Laminate absorbent cores in this configuration are described in U.S. Pat. No. 5,460,623 entitled "Trisection Sanitary Napkin" issued to Emenaker, et al. on Oct. 24, 1995. In order to provide the increased capacity in the smaller sized absorbent core used in the present invention, rather than applying a single layer of absorbent gelling material, two layers of particulate absorbent gelling material are added to the tissue layer. Preferably, a total amount of about 0.8 to about 0.9 grams of particulate absorbent material is used. A further operation is preferably performed on such a laminate absorbent core material to provide it with the desired flexibility. The laminate absorbent core can be perforated, slit, or otherwise manipulated to provide it with increased flexibility. In a preferred embodiment, the laminate absorbent core is provided with a plurality of slits oriented in the longitudinal direction to provide increased flexibility. Of course, the slits can be oriented in any other suitable direction, or in more than one direction. An example of a slit laminate absorbent core that can be modified as described above for use herein is described in U.S. Pat. No. 5,658,269 issued to Osborn, et al. on Aug. 17, 1997.

In another embodiment, the absorbent core 32 may comprise a needle punched airlaid nonwoven web. In a preferred version of such an embodiment, the needle punched airlaid nonwoven web comprises about 40% by weight of fibrous superabsorbent hydrogel-forming polymeric material and about 60% polyester fibers. (Unless otherwise stated, all percentages specified herein are based upon weight.)

In a particularly preferred embodiment, the absorbent core 32 comprises a high loft needle punched nonwoven material comprising rayon fibers and fibrous superabsorbent hydrogel-forming polymeric material. Such an absorbent core preferably comprises between about 50% to about 70%, preferably about 65% staple length viscose rayon fibers, and between about 30% and about 50%, preferably about 35% fibrous superabsorbent hydrogel-forming polymeric material. Suitable viscose rayon fibers are LYOCELL viscose rayon fibers, type 18453, obtained from Courtaulds Fibers, Inc. of North Axis, Ala. Suitable fibrous superabsorbent hydrogel-forming polymeric material is the FIBERDRI fibrous superabsorbent material discussed above. The high loft needle punched nonwoven material preferably has a basis weight of about 90 g/m$^2$. This nonwoven material is preferably needle punched with about 60 needles/cm$^2$, or more. The more needles used, the higher will be the flexibility of the finished material. Although a single layer of this high loft material can be used for the absorbent core 32, preferably at least two layers are used. More than two layers can be used, particularly if the high loft material is made in lower basis weights. The layers may be joined together, if desired. However, it has been found that the layers are adequately retained in position relative to each other when they are simply placed adjacent to each other. This is believed to be due to the fiber entanglement between the fibers on the surfaces of the layers.

In another embodiment, the absorbent core 32 may comprise a carded, thermally-bonded airlaid nonwoven web. An example of such a material comprises about 20% FIBERDRI superabsorbent material fibers, about 25% bicomponent fibers, and about 55% cellulose fluff, and has a basis weight of about 84 g/m$^2$.

The absorbent core 32 of the absorbent articles described herein can also comprise other, e.g., conventional, elements or materials. For example, any of the absorbent articles described herein may utilize an absorbent core 32 in which an underlying layer of particles or fibers of polymeric gelling agents is provided to increase the absorbent capacity of the absorbent core 32. In still other embodiments, the types of absorbent core structures like those described above can be eliminated, and a layer of particulate or fibrous superabsorbent hydrogel-forming polymeric material can be positioned along the bottom surface of the high loft topsheet material to provide the absorbent article 20 with desired absorbent capacity.

The backsheet 30 can be any suitable flexible, liquid impervious material. Preferably, the backsheet 30 is a polyethylene film having a thickness of from about 0.012 mm (0.5 mil) to about 0.015 mm (2.0 mil). Exemplary polyethylene films are manufactured by Clopay Corporation of Cincinnati, Ohio, under the designation P18-0401 and microflex 1401. The backsheet 30 may be embossed and/or matte finished to provide a more clothlike appearance.

Further, the backsheet 30 may permit vapors to escape from the absorbent core 32 (that is, it may be breathable) while still preventing exudates from passing through the backsheet. A suitable breathable backsheet material comprises an adhesively attached laminate of an apertured film having tapered capillaries, such as that described in U.S. Pat. No. 3,929,135 issued to Thompson on Dec. 30, 1975, and a microporous film. A suitable microporous film is supplied by Exxon Chemical USA, and described in Exxon's U.S. Pat. No. 4,777,073. The breathable backsheet is arranged so that the smaller openings of the tapered capillaries face the absorbent core 32. The microporous film is joined to the side of the apertured film having the larger openings to form the garment-facing surface 20B of the absorbent article.

The use of a breathable backsheet in conjunction with the menstrual panty (described in greater detail below), which preferably has a breathable crotch portion, allows the overall breathability of the system of the absorbent article and the menstrual panty to be controlled and set to an optimal level. This eliminates any variances caused by using the absorbent article randomly with commercially available undergarments that have different amounts of vapor permeability and nonpermeability.

The topsheet 28, the backsheet 30, and the absorbent core 32 may be assembled in a variety of configurations known in the art (including layered or "sandwich" configurations and wrapped or "tube" configurations). In the preferred embodiments shown in the drawings, the absorbent article 20 assembled in a sandwich construction in which the topsheet 28 and the backsheet 30 have length and width dimensions generally larger than those of the absorbent core 32. The topsheet 28 and the backsheet 30 extend beyond the edges of the absorbent core 32 to form portions of the periphery 26.

The topsheet 28 may be joined to the body-facing side of the absorbent core 32. In other embodiments, the topsheet 28 need not be joined to the absorbent core 32 to enhance the flexibility of the absorbent article 20. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The backsheet 30 need not be, and in the embodiment shown preferably is not, joined to the absorbent core 32 to enhance the flexibility of the absorbent article 20. The portions of the topsheet 28 and backsheet 30 that extend beyond the edges of the absorbent core 32 to form the periphery 26, are preferably joined to each other.

If the topsheet 28 is joined to the absorbent core 32, the topsheet 28 can be joined to the absorbent core 32 in any suitable manner known in the art for this purpose. The topsheet 28 may be joined to the absorbent core 32 by a uniform continuous layer of adhesive, a patterned layer of adhesive, or an array of separate lines, spirals, or spots of adhesive. One adhesive that has been found to be satisfactory for this purpose is manufactured by Findley Adhesive Company of Wauwatosa, Wis. as adhesive number 2031. The adhesive is preferably applied an open pattern network of filaments of adhesive such as is disclosed in U.S. Pat. No. 4,573,986 entitled "Disposable Waste-Containment Garment", which issued to Minetola, et al. on Mar. 4, 1986. Other exemplary open pattern networks of adhesive filaments comprising several lines of adhesive filaments swirled into a spiral pattern are illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the components of the absorbent article may be joined by heat bonds, pressure bonds, ultrasonic bonds, dynamic mechanical bonds, or any other suitable attachment means or combinations of these attachment means as are known in the art. The portions of the topsheet 28 and backsheet 30 that extend beyond the edges of the absorbent core 32 to form the periphery 26, can be joined to each other in any of the manners described herein.

The components of the absorbent article can be described as forming a "unitary structure." The term "unitary structure", as used herein, refers to a construction in which the components are joined together, or integrated together as a unit. The term "unitary structure" includes constructions such as those described above where the topsheet, absorbent core, and backsheet comprise separate components that are joined together. It also covers constructions in which the liquid pervious side and liquid impervious side of the absorbent articles do not comprise a separate topsheet and/or backsheet. For example, in the latter case, the liquid pervious side, the liquid impervious side, or both, may comprise a surface of the absorbent core that has the desired characteristics, rather than a separate component.

In the embodiment shown in FIGS. 1 to 3, the absorbent article 20 is provided with optional elastic members 36 that are wrapped around the longitudinal edges 22 of the absorbent article. The optional elastic members 36 form the absorbent article 20 into the desired cup-shaped configuration and provide soft longitudinal edges 22 in the event the longitudinal edges contact the wearer during use. If used, the optional elastic members 36 preferably comprise an elastomeric laminate comprising an elastomeric layer and a coverstock layer, with the coverstock layer being on the outside of the product. Suitable elastomeric laminates are described in U.S. Pat. Nos. 5,234,422 and 5,308,346 both entitled "Elasticized Sanitary Napkin" issued to Sneller, et al. on Aug. 10, 1993 and May 3, 1994, respectively.

The garment-facing surface 20B of the absorbent article 20 may include, and preferably does include a fastener for attaching the absorbent article to the specially designed supporting undergarment. Fasteners comprising adhesives, particularly pressure sensitive adhesives, which have been used to secure absorbent articles, such as sanitary napkins, to the crotch region of conventional panties can be used for this purpose.

Figure 5:
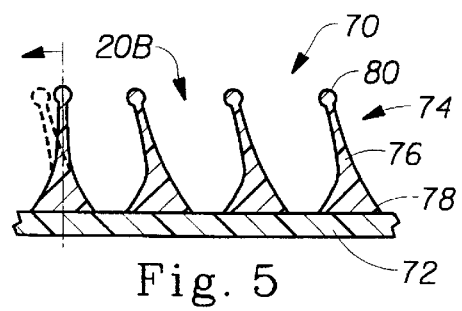
FIG. 5 is an enlarged side view of the mechanical fastening material on the garment-facing side of the absorbent article.

Preferably, however, as shown in FIGS. 2 and 3, the garment-facing surface 20B of the absorbent article 20 comprises a mechanical fastening material 70 that is particularly suitable for engaging knit materials, such as the material from which the specially designed supporting undergarment is preferably made. One type of mechanical fastening material is shown in FIGS. 2, 3, and 5. The mechanical fastening material 70 can be located on any suitable portion of the garment surface 20B. Preferably, as shown in FIG. 3, the mechanical fastening material 70 is located on the entire portion of the garment-facing surface 20B that lies between the optional elastic members 36. In other embodiments, the mechanical fastening material 70 could cover all, or any other suitable portion of the garment-facing surface 20B of the absorbent article, including the elastic members 36.

The mechanical fastening material 70 shown in FIGS. 2, 3, and 5 comprises a substrate or surface 72 with an array of prongs in the form of a plurality of small filamentous (or hair-like) projections 74 extending therefrom. The hair-like projections 74 may be of any suitable shape. FIG. 5 shows one preferred shape of the projections 74 in greater detail. The hair-like projections 74 may, but need not, have a hook shape like conventional VELCRO hook fastening material. In the embodiment shown in FIG. 5, the hair-like projections 74 preferably do not have a hook shape. The hair-like projections 74 preferably have a straight shank 76 that tapers so that it generally decreases in diameter from the base 78 of the shank 76 toward the distal end of the shank. More specifically, the shank 76 decreases in diameter from the base 78 of the shank 76 toward the distal end of the shank until about the mid-point of the shank. The diameter of the shank 76 remains constant from about the mid-point of the shank to the distal end of the shank 76. The distal end of the shank 76 preferably has a small spherical engaging means 80 thereon. The hair-like projections 74 in the preferred embodiment shown in the drawings preferably extend at a slight angle from an orientation that is perpendicular (that is, at an angle of about 90 degrees) from substrate. Preferably, the hair-like projections 74 are oriented at an angle that is about 10° less than a perpendicular orientation relative to the substrate.

The mechanical fastening material 70 can be distributed in any suitable pattern across the garment surface 20B. In a particularly preferred embodiment, as shown in FIG. 3, the mechanical fastening material 70 is distributed in several zones (e.g., three zones, each about 0.75 inches (about 2 cm) wide) in which the orientation of the hair-like projections differs between adjacent zones. More specifically, in the embodiment shown in FIG. 3, the hair-like projections in a central zone that runs along the longitudinal centerline L are oriented at an angle that is about 10° less than a perpendicular orientation relative to the substrate which is oriented toward one end of the absorbent article. The hair-like projections in the adjacent longitudinal side zones form a similar angle relative to the substrate, but they are oriented toward the opposite end edge of the absorbent article 20. The orientation of the hair-like projections in these different zones is shown by arrows in FIG. 3.

Figure 6:
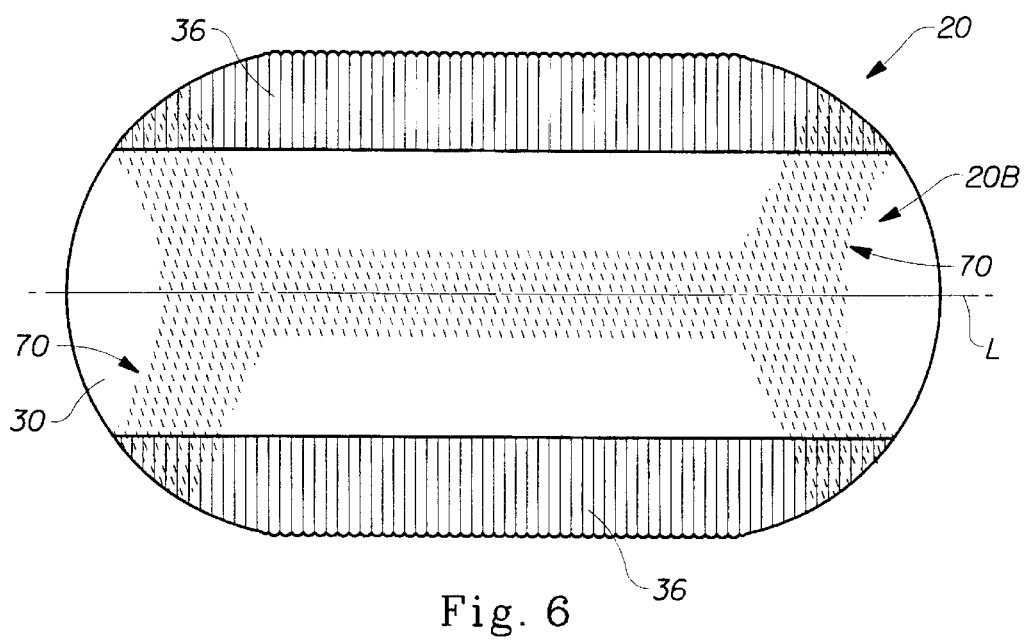
FIG. 6 is a bottom plan view of an embodiment of the absorbent article of the present invention which has mechanical fastening material on the garment-facing side which is arranged in a pattern that is complementary with portions of the menstrual undergarment shown in the following figures.

In other embodiments, the mechanical fastening material 70 can be distributed in a pattern that matches the pattern of one or more pre-selected portions of the specially designed supporting garment. For example, the mechanical fastening material 70 can be arranged in a pattern that corresponds to and aligns with the longitudinal stretch control member 52 and/or the angled stretch control members 54 of the menstrual undergarment 38 shown in FIGS. 7 and 8. (The menstrual undergarment is described in greater detail below.) For instance, as shown in FIG. 6, portions of the mechanical fastening material 70 at each end of the absorbent article can be arranged in a chevron pattern to correspond to the angled stretch control members 54 of the menstrual undergarment. In a variation of this embodiment, the mechanical fastening material 70 and/or the other portions of the supporting garment could be designed so that the mechanical fastening material 70 will not engage other than with a particular portion of the supporting garment, such as the longitudinal or angled stretch control members. The alignment of the mechanical fastening material 70 with these portions of the supporting garment can be used as a placement aid to ensure that the absorbent article 20 is positioned properly in the supporting garment. The pattern of mechanical fastening material 70 can also be used to assist the absorbent article 20 in fitting closely against the wearer's body in certain areas.

The mechanical fastening material 70 shown in FIG. 5 provides the garment surface 20B of the absorbent article with a fastener that is capable of easily adhering to knit material, and has a sufficiently high holding force even if the supporting garment stretches and contracts. The mechanical fastening material 70 described herein is particularly preferred for use with the specially designed knit supporting undergarment since it will not become detached when the supporting garment stretches and contracts during application of the absorbent article to the undergarment, as will some pressure sensitive adhesives.

The mechanical fastening material 70 can be made by printing or spraying a material to form small nubs on a surface or a substrate, such as a film. The nubs are then formed into the projections 74. The substrate 72 can be of any thickness or density. The substrate 72 can even include relatively rough or corrugated sections, such as the regions of the optional elastic members 56 that are formed into gathered portions. The mechanical fastening material 70 described herein is particularly useful because it can be printed directly on substrates such as the backsheet. Alternatively, the mechanical fastening material can be printed on a separate component that is joined to a portion of the absorbent article. In the preferred embodiment shown in the drawings, however, the substrate to which the mechanical fastening material is applied is the garment-facing side 20B of the absorbent article.

The material that is used to form the nubs can be any suitable material that can be printed or sprayed on the substrate and formed into the projections- described herein. Suitable materials include, but are not limited to thermal plastics and hot melt resins. The material used to form the projections 74 can be applied by any suitable printing or spray method (e.g., spiral, mist, line spraying, or gravure, rotary screen, or flexographic printing). Methods suitable for forming the projections 74 of the fastening material 70 are described in greater detail in U.S. Pat. No. 5,392,498 issued to Goulait, et al. on Feb. 28, 1995. The projections 74 can have any suitable cross-sectional shape, including but not limited to oval, round, diamond, and pyramidal shapes. The print or spray pattern can be applied in any suitable pattern that produces dots, circles, lines, dimples, and the like, or it can comprise a combination of patterns. The material can be printed in regular or random patterns. The projections 74 formed thereby preferably extend outward a distance of about 0.05 mm to about 3 mm from the surface of the substrate 72.

In the embodiment described above, the substrate 72 is a polyethylene film backsheet material and the printing resin is polyester. Two suitable polyester resins that can be used for this purpose are a resin known as A-3 obtained from Eastman Chemical Products, Inc. of Kingsport, Tenn. and a resin known as CA-X105 obtained from Century International Adhesives and Coatings Corporation of Columbus, Ohio. The latter polyester resin has a tackifier therein to provide the mechanical fastening material with higher adhesive tack. This aids the mechanical fastening material 70 in adhering to the supporting undergarment. In this preferred embodiment, the mechanical fastening material 70 is printed by a rotary screen printing process. The printing can take place at any suitable stage in the manufacture of the absorbent article.

The polyester resin can be printed so that the hair-like projections 74 are distributed in any suitable density. Preferably, the projections 74 are distributed in the densities described in U.S. Pat. No. 5,392,498 issued to Goulait, et al. referred to above. More preferably, the hair-like projections 74 are distributed in densities that are at, or above, the higher end of the range described in the Goulait, et al. patent. For example, in preferred embodiments, the hair-like projections 74 are preferably distributed so that there are about 105 rows of projections in both the longitudinal and transverse directions per square inch (or about 11,000 projections per square inch).

In another embodiment, the mechanical fastening material 70 can comprise a material having a "T"-shaped or mushroom-shaped appearance when viewed from the side. One particularly preferred "T"-shaped mechanical fastening material for use on the absorbent article of the present invention is a material known as TP200 available from 3M Personal Care and Related Products Division of Menomonie, Wis.

The mechanical fastening materials 70 described herein differ in several respects from conventional mechanical fastening material, such as VELCRO hook material and other fasteners commonly used on absorbent articles, such as adhesive fasteners. The mechanical fastening material 70 does not require a mating loop fastening component like VELCRO hook material. The mechanical fastening material can, instead, directly engage the fabric of the supporting undergarment. The mechanical fastening material 70 used on the absorbent article of the present invention further differs from conventional mechanical fasteners due to the fact that it has projections that are substantially smaller than conventional VELCRO hooks. The projections are virtually unnoticeable to the wearer's eye. The mechanical fastening material 70 used in the present invention has improved tactile properties due to the small size and close spacing of the projections. As a result of the small size and close spacing of the projections, if the wearer comes into contact with these projections, they tend to only feel the tips of the projections so that the mechanical fastening material tends to have a velvet-like feel.

The mechanical fastening materials 70 described herein are smoother, softer, and more flexible than conventional VELCRO fastening material. The mechanical fastening materials, therefore, are less offensive (scratchy) than conventional VELCRO fastening material. The mechanical fastening materials 70, since they can be printed directly on a substrate, can also utilize a greater variety of substrates (and are especially preferred for use with more flexible substrates). The mechanical fastening material 70 can, in some embodiments, also maintain the garment surface 20B in place by friction and/or by adhesive attachment, in addition to the mechanical engagement.

However, even when the mechanical fastening material 70 is provided with an adhesive-like tack, there is generally no need to apply separate release papers to cover the fastening material 70, as with conventional pressure sensitive adhesives. Thus, the usual inconvenience of handling and disposing of such release papers is eliminated. In addition, the use of the mechanical fastening material avoids certain undesirable tendencies associated with the wearing of absorbent articles having adhesive fasteners on their garment surface. For example, the mechanical fastening material eliminates the tendency of the adhesive on the garment-facing side of an absorbent article to stick to itself and/or to the wearer's body. This is potentially a problem when the absorbent article is first placed in use. It is also potentially a problem during wear if the adhesive fastener should come unfastened from the wearer's undergarment, such as when the wearer pulls down the undergarment to check the absorbent article and during vigorous motions by the wearer.

In addition to the mechanical fastening material described above, and pressure sensitive adhesives, the garment-facing side 20B of the absorbent article 20 may employ other alternative types of fasteners. In one non-limiting example, the absorbent article 20 can be provided with a cohesive material that adheres to a cohesive material on the inside of the crotch portion of the supporting undergarment. As used herein, a "cohesive material" is one which preferentially adheres to itself and not to other materials. Such a material can be used as a placement aid to ensure that the absorbent article 20 is positioned properly in the supporting garment.

Figure 7:
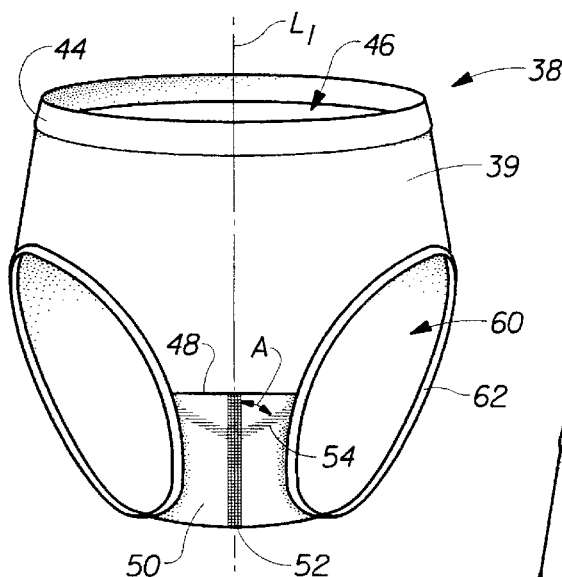
FIG. 7 is a front view of a preferred embodiment of a menstrual undergarment for use with the absorbent article of the present invention.
Figure 8:
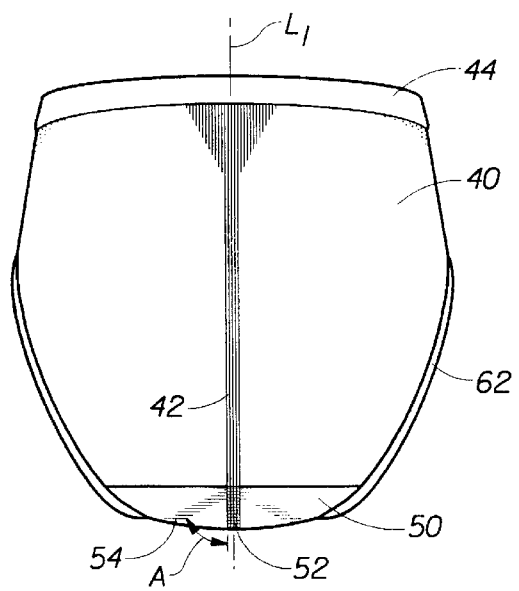
FIG. 8 is a rear view of a preferred embodiment of a menstrual undergarment for use with the absorbent article of the present invention.

FIGS. 7 and 8 show front and rear views of a supporting garment in the form of a menstrual undergarment 38 that is preferred for use with the present invention. As is shown in FIGS. 7 and 8, the menstrual undergarment 38 comprises a front portion 39 which may be in the form of a front panel, a rear portion 40 which may be in the form of a rear panel, a crotch region or portion 50 which may be in the form of a crotch panel, a pair of leg openings 60 which may be elasticized, and an elasticized waistband 44. The menstrual undergarment 38 is also provided with a waist opening 46 allowing entry into the menstrual undergarment 38. The menstrual undergarment 38 further comprises an extensible lifting member such as lifting strip 42 disposed along the longitudinal centerline $L_1$ in the rear portion 40, a longitudinal stretch control member 52 disposed along the longitudinal centerline in the crotch portion 50, and a plurality of angled stretch control members 54 disposed at an angle A with respect to the longitudinal stretch control member 52 and extending therefrom to the leg elastics 62. It should be noted that any seam or gusset 48 at the front end of the crotch portion 50 is preferably situated so that it lies under or behind (that is, rearward of) the pubic bone so that the pubic bone does not interfere with the fit of the menstrual undergarment. It should also be understood that any or all of the features of the menstrual undergarment 38 described herein may be knit into the menstrual undergarment, and need not comprise sewn together portions of the menstrual undergarment.

Figure 16:
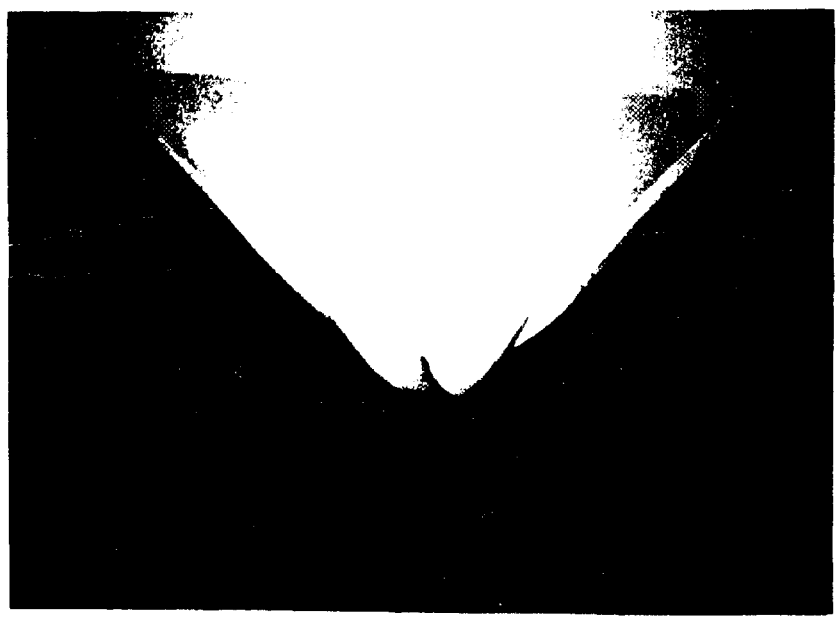
FIG. 16 is a frontal photograph which shows one example of how the menstrual undergarment for use with the absorbent article of the present invention fits when the wearer's legs are together.
Figure 15:
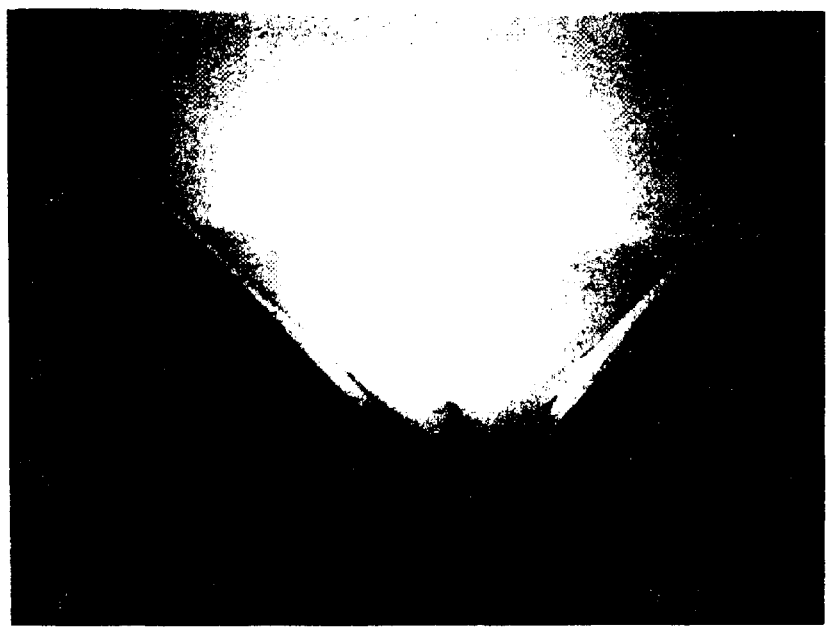
FIG. 15 is a frontal photograph which shows one example of how the menstrual undergarment for use with the absorbent article of the present invention fits when the wearer's legs are apart.

The absorbent article 20 is utilized by placing the absorbent article 20 in the crotch portion of the menstrual undergarment 38. The absorbent article 20 is placed in the crotch portion of the menstrual undergarment with one end extending toward the front section of the menstrual undergarment and the other end towards the back section of the menstrual undergarment. The backsheet 30 is placed in contact with the inner surface of the center of the crotch portion 50 of the menstrual undergarment. The hair-like projections 74 of the mechanical fastening material 70 on the garment-facing side 20B of the absorbent article engage with the knit material from which the crotch portion 50 of the menstrual undergarment 38 is made. The wearer then pulls on the menstrual undergarment 38. The menstrual undergarment 38 will typically stretch and contract, until it fits as shown in FIGS. 15 and 16.

Figure 9:
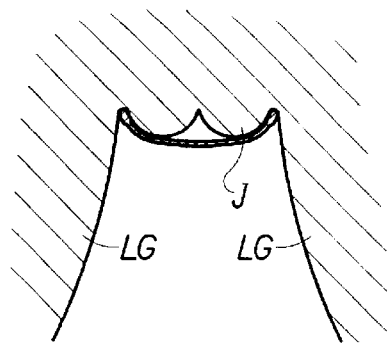
FIG. 9 is a cross-sectional view taken transversely through a portion of a wearer's body which shows how a prior art conventional pair of panties often fit when the wearer's legs are apart.
Figure 10:
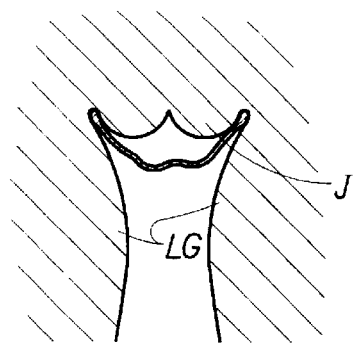
FIG. 10 is a cross-sectional view taken transversely through a portion of a wearer's body which shows how a prior art conventional pair of panties often fit when the wearer's legs are together.
Figure 14:
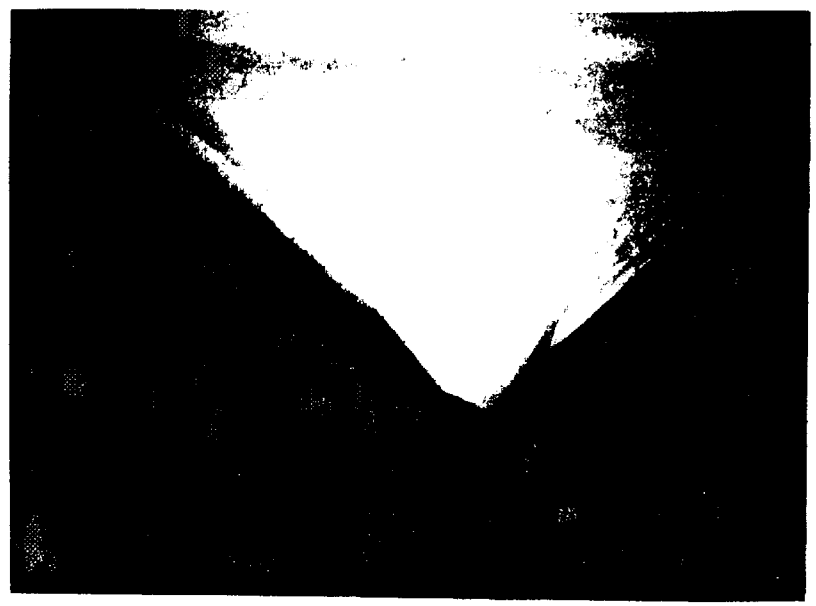
FIG. 14 is a frontal photograph which shows how a prior art conventional pair of panties often fit when the wearer's legs are together.
Figure 13:
FIG. 13 is a frontal photograph which shows how a prior art conventional pair of panties often fit when the wearer's legs are apart.

FIGS. 9 and 10, respectively, show examples of how a conventional prior art pair of panties fits in the crotch region when the wearer's legs, LG, are apart, and when they are brought together. As shown in FIG. 9, when the wearer's legs are apart, the crotch region of a conventional pair of panties "gaps" along a longitudinally oriented area centered about the space between the wearer's labia (which are designated by reference letter J). As shown in FIG. 10, the crotch region of these conventional panties sag when the wearer's legs are brought together. A similar comparison is shown photographically in FIGS. 13 and 14. FIG. 13 shows how a conventional pair of panties fits in the crotch region when the wearer's legs are apart. FIG. 14 shows how the panties fit when the wearer's legs are brought together.

Figure 11:
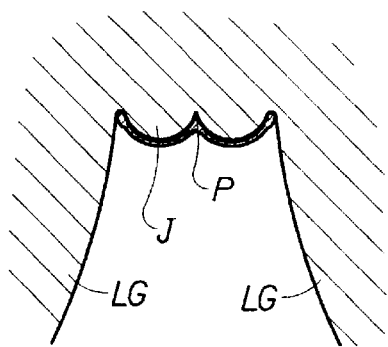
FIG. 11 is a cross-sectional view taken transversely through a portion of a wearer's body which provides one example of how the menstrual undergarment used with the absorbent article of the present invention fits when the wearer's legs are apart.
Figure 12:
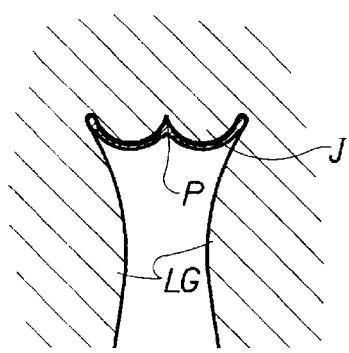
FIG. 12 is a cross-sectional view taken transversely through a portion of a wearer's body which provides an example of how the menstrual undergarment used with the absorbent article of the present invention fits when the wearer's legs are together.

The menstrual panty as shown schematically in FIGS. 11 and 12, on the other hand, comfortably fits against and conforms to the inside and outside surfaces of the labia majora whether the wearer's legs are apart, or together. The menstrual panty maintains the coverage of the desired areas of the wearer's body without applying significant "girdle-like" forces. As shown in FIGS. 11 and 12, in cross-section, the menstrual panty preferably maintains a modified cusp-shaped configuration in this area throughout a range of body motions (that is, dynamically). A similar comparison is shown photographically in FIGS. 15 and 16. The cross-sectional configuration of the menstrual panty is described as being a "modified" cusp-shape because it may, but preferably does not form a point, P, where the curved portions of the cusp-like shape meet in the longitudinally-oriented area in the space between the wearer's labia, but is more rounded, and preferably convex in this area.

The menstrual panty fits against the wearer's body so closely, particularly in the crotch region, that it is like a comfortable "second skin". The absorbent article 20 preferably does not alter or override the tendency of the menstrual panty to achieve this "second skin" fit. The absorbent article 20 is preferably sufficiently flexible so that it assumes a configuration similar to the crotch region of the menstrual panty. Preferably, the absorbent article 20 also conforms to the shape of the wearer's pudendal region in use. The absorbent article preferably conforms to the shape of the wearer's pudendal region regardless of whether the wearer's legs are together or apart.

The absorbent article 20 preferably flexes under the forces applied by the menstrual panty 38 that are used to hold the absorbent article comfortably against the wearer's body. If the absorbent article flexes under these forces, it will not override the tendency of the menstrual panty to achieve the desired fit, and the absorbent article 20 will assume a shape similar to the crotch region of the menstrual panty 38. The menstrual panty 38 described herein preferably applies body-contacting pressures to the wearer's body of less than or equal to about 20 $g/cm^2$, more preferably less than or equal to about 15 $g/cm^2$. A body-contacting pressure of 20 $g/cm^2$ applied by the menstrual panty 38, is a pressure which is high enough that it is on the borderline of being uncomfortable for the wearer.

It is recognized that there are other garments, such as Japanese menstrual shorts, that are close fitting. However, such garments tend to apply forces that uncomfortable, particularly on the wearer's legs at those places where the wearer's legs are contacted by the elasticized edges of the menstrual shorts. The menstrual panty 38 described herein, on the other hand, is particularly preferred because it is capable of applying body-contacting forces along the crotch region thereof which keep the absorbent article 20 in close contact with the wearer's pudendal region without creating uncomfortable forces on the wearer's legs (greater than or equal to about 20 $g/cm^2$) at the places where the wearer's legs are contacted by the leg openings of the menstrual panty 38. Preferably, the edges of the crotch region of the menstrual panty described herein apply a body-contacting pressure to these regions of the wearer's body that is less than or equal to about 20 $g/cm^2$.

The absorbent article 20 and menstrual panty 38 also differ from prior sanitary napkins and conventional underwear in the sustained nature of the contact of the absorbent article with the wearer's body. Some current sanitary napkins may occasionally assume a "W"-shaped cross sectional configuration during wear, such as when the wearer is sitting. However, conventional underwear does not provide a constant force against the wearer's body to hold the sanitary napkin in place under all circumstances, such as when the wearer is walking or standing, or when the wearer's legs are apart. The absorbent article 20 and the menstrual panty 38, on the other hand, provide such sustained contact with the wearer's body. The absorbent article may be described as being substantially maintained in sustained contact with the wearer's body, in which case the absorbent article need not be in complete and/or continuous contact with the wearer's body, but is maintained in contact with the wearer's body more than it is out of contact with the wearer's body.

The absorbent article 20 preferably is capable of maintaining contact with and covering at least a portion of the inside surfaces of the wearer's labia, the exterior surfaces of the wearer's labia, and the menstrual panty 38. The absorbent article 20 preferably covers an area centered about the wearer's labia having projected width of at least about 1 inch (about 2.5 cm). The absorbent article may cover substantially all of the interior surfaces of the wearer's labia up to and including contacting and covering the floor of the wearer's vestibule. The absorbent article may also cover substantially all of the exterior surfaces of the wearer's labia.

Another way of describing the configuration the absorbent article 20 may take during wear is by looking at the different regions of the absorbent article 20. The absorbent article 20 preferably has a longitudinal central region centered about its longitudinal centerline, L, that is capable of being positioned in the space between the wearer's labia. This longitudinal central region may be of any suitable width that is less than the width of the entire absorbent article. The longitudinal central region may, for example, correspond to the size and location of the tube of absorbent material 90 shown in FIG. 24. The longitudinal central region may extend the full length of the absorbent article 20, or less than the full length of the absorbent article. The longitudinal central region preferably has at least a portion (typically along the longitudinal centerline of the absorbent article) that is capable of residing in the space between the wearer's labia at an elevation that is higher (when the wearer is standing) than at least some portions of the absorbent article that are located laterally outboard of the longitudinal central region. The absorbent article 20 is preferably capable of assuming such a configuration without compression by the inner portions of the wearer's thighs.

Figure 17:
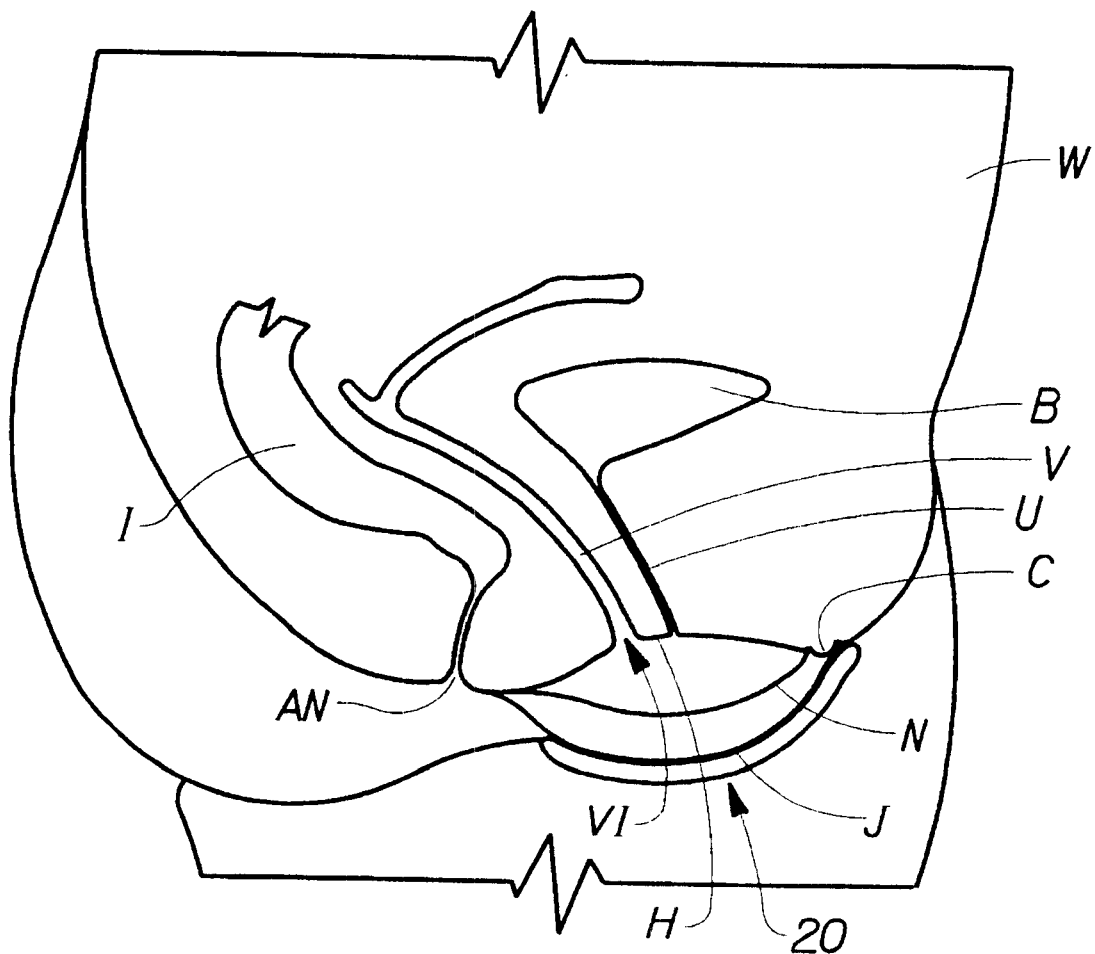
FIG. 17 is a cross-sectional sagital view of a human female wearer showing the absorbent article of the present invention in place.

FIG. 17 shows a preferred embodiment of the absorbent article 20 of the present invention worn against the body of a wearer W. The urogenital members shown in FIG. 17 include the bladder B, the vagina V, the urethra U, the clitoris C, the large intestine I, the anus AN, the vaginal introitus VI, the hymeneal ring H, the labia minora N, and the labia majora J. FIG. 17 shows one example of the relationship of these anatomical features of the wearer W to the absorbent article 20 when the absorbent article is properly worn.

The absorbent article 20 preferably cups the labia from front to back. The absorbent article 20 shown in FIG. 17 is preferably sufficiently small that it only covers the wearer's pudendal region and immediately adjacent regions, and in particular, covers the vaginal introitus and the surfaces of the labia majora. The absorbent article 20 may also cover the wearer's perineum. The absorbent article 20 shown in FIG. 17 preferably does not extend appreciably beyond these parts of the wearer's body. The absorbent article may cover the wearer's clitoris, but preferably does not extend substantially forward beyond the wearer's mons pubis. The absorbent article 20 may be spaced slightly away from the clitoris, or it may fit closely against the clitoris, as it does relative to the other regions of the wearer's body. The absorbent article 20 preferably does not extend rearward to contact the wearer's anus to avoid sensitive nerve endings therein. When the absorbent article 20 is of this preferred size, it provides a more comfortable, and less noticeable absorbent article since it occludes less of the crotch region of the wearer's body and allows air to circulate around the same.

The absorbent article 20 also preferably does not cover areas of the wearer's body that undergo substantial degrees of movement (that is, the absorbent article will only be placed adjacent to "low motion zones" of the wearer's body). In particular, it is desirable that the side edges of the absorbent article 20 will not be contacted by the inside surfaces of the wearer's thighs when the wearer walks, or otherwise moves about. This overcomes a drawback of conventionally-sized sanitary napkins and pantiliners, which being comparatively stiff relative to the absorbent article 20 of the present invention, will transfer forces applied to the edges thereof to other portions of the sanitary napkin or pantiliner, causing the same to bend or crumple, and/or shift from the desired position under the wearer's vaginal introitus.

The absorbent article 20 of the present invention can be made somewhat larger if the edge portions thereof which may be contacted by the inside surfaces of the wearer's thighs, LG, do not translate forces acting thereon to the remainder of the absorbent article so as to cause the absorbent article to bend or crumple, and/or shift from the desired position under the wearer's vaginal introitus. For example, it is also contemplated herein that an absorbent article 20 can be constructed which has the desired flexibility, fit, and an absorbent region with the preferred small size described herein (e.g., covering the pudendal region and the perineum), but which has regions that are located outboard of these regions which merely serve a "drop cloth" function, which have minimal or no absorbency. For instance, such regions could be comprised only of topsheet and backsheet materials, and possibly a thin layer of absorbent material therebetween. It is considered that such an embodiment will also fall within the scope of the present invention.

Alternatively, the absorbent article 20 of the present invention can have a region, typically in the center thereof, that is stiffer than the portions of the absorbent article that lie outboard of this center region. In other words, the absorbent article 20 may have a central low motion area which has a greater thickness and less flexibility than the regions of the absorbent article that are in higher motion areas (the higher motion areas are those areas which might be contacted by the insides of the wearer's thighs). In each of these embodiments, the absorbent article 20 preferably does not shift more than about 1.5 inches (about 3.8 cm), more preferably about 1 inch (about 2.5 cm), and most preferably about 0.5 inch (about 1.3 cm) from its position relative to the wearer's vaginal introitus when the absorbent article 20 is worn in the supporting garment during the following protocol.

For the purposes of determining how far the absorbent article shifts relative to the wearer's vaginal introitus, a five minute walking protocol is used. The wearer should place the absorbent article in the menstrual undergarment, and pull the menstrual undergarment in place. The wearer can then indicate where her vaginal introitus is by pointing with her finger to the outside surface of the menstrual undergarment. This portion of the undergarment is marked with a suitable washable felt tip marker. If desired, marks can also be made on one or more portions of the periphery of the absorbent article 20, and corresponding marks can be made on the immediately adjacent portions of the wearer's body. The wearer then walks normally for five minutes. After this period of walking, the wearer again indicates where her vaginal introitus is, and this position is marked. The distance that the marks are apart after the wear cycle is the amount that the absorbent article has shifted.

Figure 18:
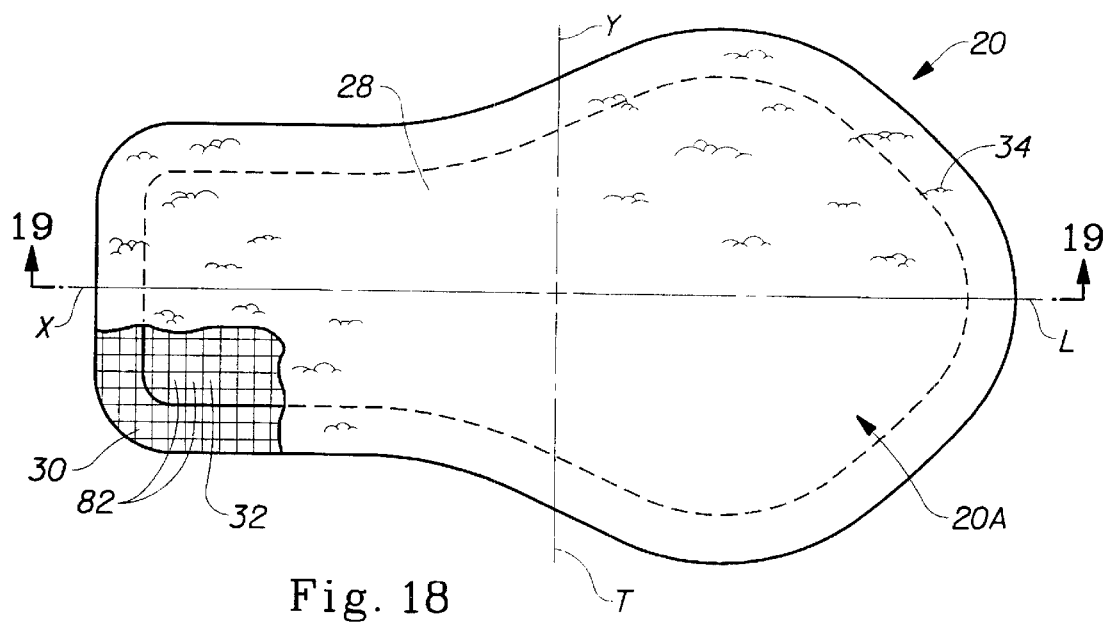
FIG. 18 is a partially fragmented top plan view of another embodiment of the absorbent article of the present invention.
Figure 19:
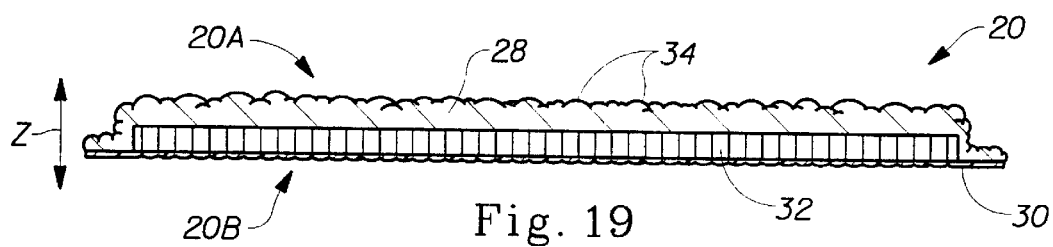
FIG. 19 is a cross-sectional view of the absorbent article shown in FIG. 18 taken along line 19—19 of FIG. 18.
Figure 20:
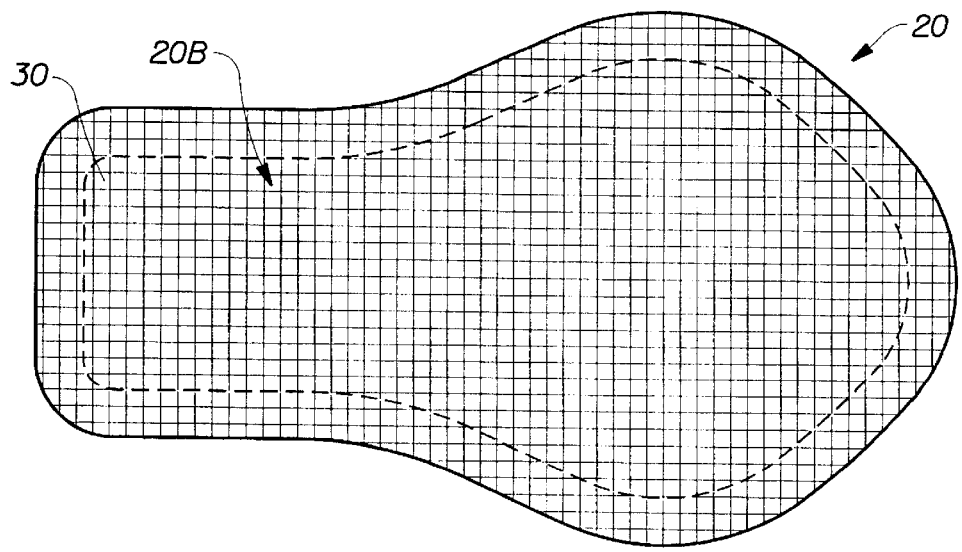
FIG. 20 is a bottom plan view of the absorbent article shown in FIG. 18.

Other embodiments of the absorbent article described herein are also possible. For example, FIGS. 18–20 show another embodiment of the absorbent article 20 of the present invention in which the absorbent core 32 comprises absorbent material arranged in a flexible structure, preferably a highly flexible structure. In order to arrange the absorbent core 32 into a flexible structure, the absorbent core 32 is preferably either: slit, in the form of strands, particles, or a plurality of columns. The absorbent material can be any suitable absorbent material that is capable of being formed into such a structure. Suitable absorbent materials that are capable of being formed into such a structure include, but are not limited to, nonwoven materials, such as thermally bonded air laid nonwoven materials, absorbent sponges, and absorbent foam materials.

Preferred thermally bonded air laid materials are described in U.S. Pat. No. 5,607,414 entitled "Catamenial Absorbent Structures Having Thermally Bonded Layers For Improved Handling of Menstrual Fluids, and Their Use in Sanitary Napkins Having Improved Fit and Comfort" issued to Richards, et al. on Mar. 4, 1997.

In the embodiment shown in FIGS. 18–20, the absorbent core 32 preferably comprises a highly porous absorbent HIPE polymeric foam that is formed into a plurality of particles or upright, spaced apart columns of foam material 82. Suitable absorbent HIPE foam materials are described in U.S. Pat. No. 5,260,345 issued to DesMarais, et al. on Nov. 9, 1993; U.S. Pat. No. 5,268,224 issued to DesMarais, et al. on Dec. 7, 1993; U.S. Pat. No. 5,387,207 issued to Dyer, et al. on Feb. 7, 1995; U.S. Pat. No. 5,550,167 issued to DesMarais on Aug. 27, 1996; U.S. Pat. No. 5,563,179 issued to Stone, et al. on Oct. 8, 1996; U.S. Pat. No. 5,650,222 issued to DesMarais, et al. on Jul. 22, 1997; and allowed U.S. patent application Ser. No. 08/542,497 filed Oct. 13, 1995, by Dyer, et al. (P&G Case 5546R). Such absorbent foam materials are particularly preferred because they can be provided with good resistance to compression and exhibit good resiliency following compression. The absorbent foam materials described in these different patents may also be tailored so that they are provided with the ability to absorb particular types of bodily exudates (e.g., menses and/or urine).

The absorbent article 20 shown in FIGS. 18–20 can be formed by adhesively attaching one of the preferred high loft fibrous materials described above to one side of the foam absorbent material, and one of the backsheet materials (described herein) to the other side of the absorbent foam material to form a composite web. The composite web is then preferably mechanically strained as described in greater detail below. This will slit the absorbent foam material. The process for mechanically straining the absorbent foam material, however, will not destroy the integrity of the high loft topsheet material or the backsheet, and will provide a self-contained slit or particulate absorbent foam material between the topsheet 28 and backsheet 30.

If the thickness of the absorbent foam material is greater than the dimensions into which the web of absorbent foam material is cut, then the mechanical straining process (described below) will form the absorbent foam material into a plurality of columns of absorbent material. The absorbent material may, thus, be referred to herein as comprising "columnar" material. The term "columnar", as used herein, refers to absorbent structures comprising more than one, and preferably a plurality of three dimensional elements having a pair of ends, a height, and a cross-sectional area, wherein the ratio of the height to the dimensions of the cross-sectional area (the aspect ratio) is greater than 1:1.

To complete the formation of the absorbent article 20 shown in FIGS. 18–20, the topsheet 28 and backsheet 30 are preferably peripherally joined (outboard of the absorbent foam material). The topsheet 28 and backsheet 30 can be joined to each other about their peripheries in any suitable manner, including, but not limited to: crimping, heat and/or pressure bonding, adhesives, and double-sided adhesive tapes.

Numerous variations of the alternative embodiment shown in FIGS. 18–20 are possible. For example, the topsheet of the embodiment shown in FIGS. 18–20 can be removed, and the absorbent foam material can be placed directly against the wearer's body. The absorbent foam material, particularly if it is in the form of columnar material, can provide a plurality of Z-direction oriented columns of absorbent material that can adjust to the body contours of individual women, and fit within the spaces between the wearer's pubic hair to break the flow of menses along the wearer's body.

Figure 21:
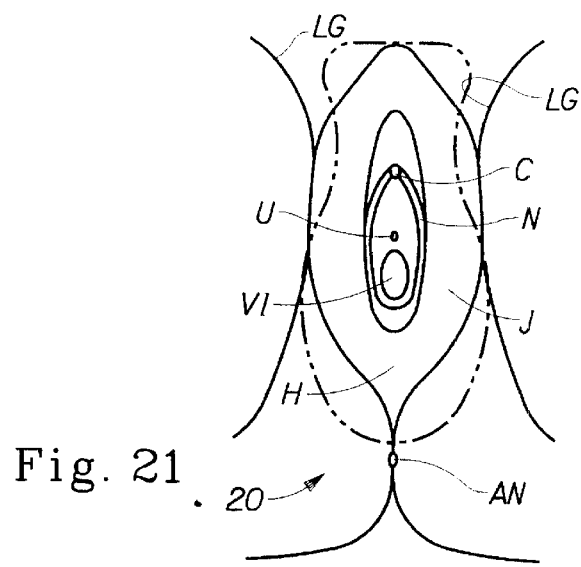
FIG. 21 is a view of the wearer's pudendal region showing the absorbent article shown in FIGS. 18–20 in place.

FIG. 21 shows one non-limiting example of the manner in which the key hole-shaped absorbent article 20 shown in FIGS. 18–20 may fit adjacent to the wearer's body. As shown in FIG. 21, the absorbent article 20 has a rounded or oval portion and a generally rectangular extension therefrom. The key-hole shaped absorbent article 20 can worn with either end placed at the front of the wearer's body. Preferably, however, the key-hole shaped absorbent article 20 is worn with the rectangular extension at the front of the wearer's body, and the wider rounded or oval portion at the rear of the wearer's body. The wider rounded or oval portion can bend upward to fit into the crevice between the wearer's buttocks (the "gluteal groove"), and the extra width still provides an adequate degree of coverage of the menstrual panty.

Figure 22:
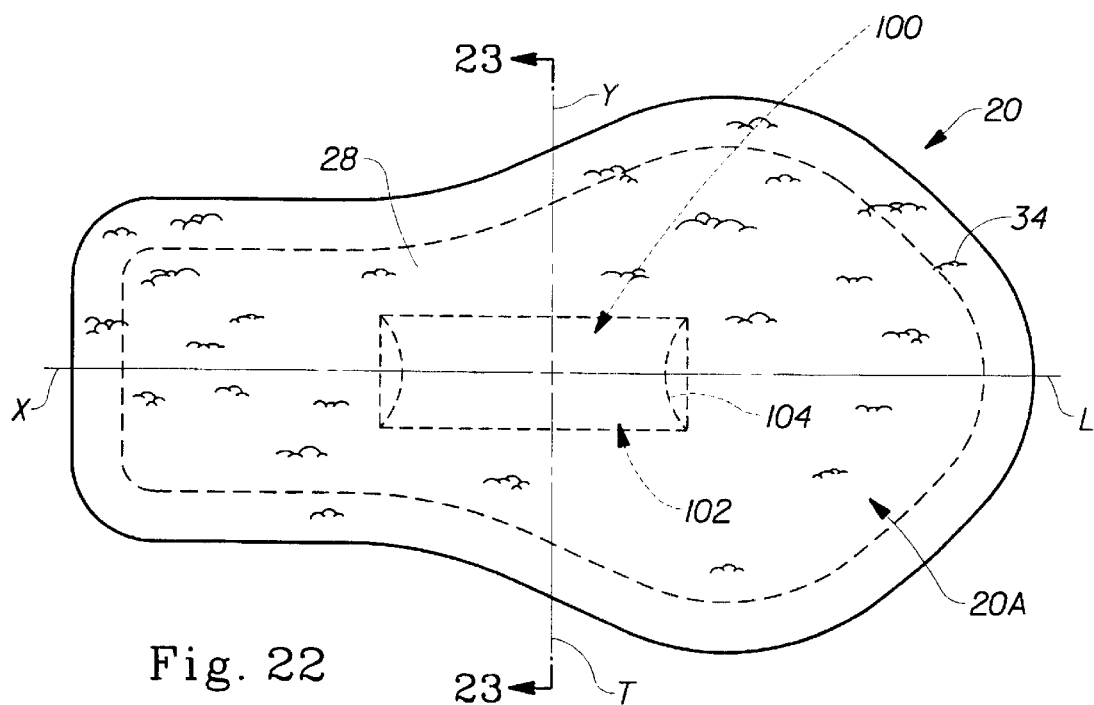
FIG. 22 is a top plan view of an alternative embodiment of the absorbent article of the present invention having a hump-forming insert on its body-facing side.
Figure 23:
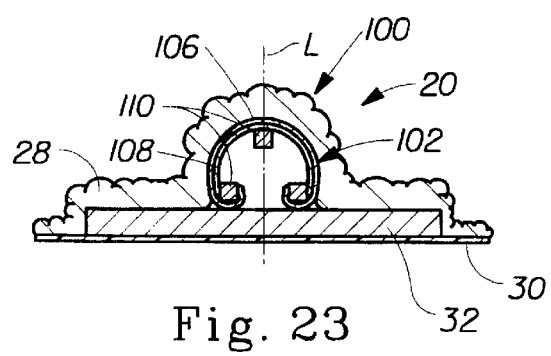
FIG. 23 is a cross-sectional view of the absorbent article shown in FIG. 22, taken along line 23—23 of FIG. 22.

FIGS. 22 and 23 show another embodiment of the absorbent article of the present invention. The embodiment shown in FIGS. 22 and 23 is intended to provide the absorbent article with an increased ability to intercept liquid bodily exudates at the location of the wearer's body that is the source of the exudates.

The embodiment shown in FIGS. 22 and 23 preferably comprises a key hole-shaped base pad similar to that shown in FIGS. 18–20. The absorbent core may, but need not, comprise a plurality of particles of absorbent foam material. The absorbent core in this embodiment can comprise any of the high efficiency absorbent core materials described herein. Preferably in the embodiment shown in FIGS. 22 and 23, (although shown schematically as a single layer) the absorbent core comprises two layers of a nonwoven web comprising a blend of from about 60% to about 90%, preferably about 75%, viscose rayon fibers, and from about 10% to about 40%, preferably about 25%, FIBERDRI superabsorbent material fibers obtained from Camelot Technologies Ltd.

The absorbent article shown in FIGS. 22 and 23 further comprises a longitudinally-oriented central absorbent hump 100 on its body-facing side. The hump 100 is formed by a hump-forming element (or "insert") 102 that is preferably inserted between the highloft topsheet 28 and the absorbent core 32.

The hump-forming element 102 is sized to fit completely with the wearer's interlabial space. In one preferred embodiment, the hump-forming element 102 has a length as measured along its base of about 50 mm. As shown in FIG. 22, the hump-forming element has a top portion that has its ends 104 rounded off (especially apparent when viewed from the side) for improved comfort. The length of the top portion as measured where this rounding commences is preferably about 40 mm. The hump-forming element 102, in this embodiment, preferably has a maximum height or caliper of about 20 mm. The width of the hump-forming element 102 as measured at its base is preferably about 20 mm.

In this particular embodiment, as shown in FIG. 23, the insert 102 comprises several elements. These include a first web of material such as first folded web of absorbent material 106, an underlying layer 108, and several pieces of resilient material 110.

The first folded web of absorbent material 106 preferably comprises, a material that is capable of quickly moving bodily exudates away from the wearer's body. In the embodiment shown in FIGS. 22 and 23, the first web of material 106 may comprise a hydroentangled nonwoven web comprised of natural fibers, polymeric fibers, co-polymeric fibers, or mixtures thereof. A suitable material for the first folded web 106 is known as FIBRELLA-Suominen made by J. W. Suominen Oy of Nakkila, Finland. The first folded web of absorbent material 106 is preferably gradually bent or is folded about a plurality of longitudinally-oriented folding lines into the cross-sectional configuration shown in FIG. 23. As shown in FIG. 23, the first folded web 106 has an inverted U-shaped configuration along its longitudinal centerline. The longitudinal side margins of the first folded web are folded inward and upward inside the inverted U-shaped portion of the folded web to define two smaller U-shaped portions.

The underlying 108 layer preferably comprises a material that is capable of drawing liquids away from the first folded web of absorbent material 106 and storing such liquids. In the embodiment shown in FIGS. 22 and 23, the underlying layer 108 preferably comprises a thermally bonded wet laid nonwoven web. Suitable thermally bonded wet laid nonwoven webs are described in U.S. Pat. No. 5,549,589 entitled "Fluid Distribution Member for Absorbent Article Exhibiting High Suction and High Capacity" issued to Horney, et al. on Aug. 27, 1996. The underlying layer 108 in the embodiment shown in FIGS. 22 and 23, is narrower in width than the first folded web of absorbent material 106 and terminates short of the longitudinal side margins of the first folded web of absorbent material 106 so that it underlies only the inverted U-shaped portion of the first folded web of absorbent material 106. The underlying layer 108 may or may not be joined to the first folded web of absorbent material 106.

The pieces of resilient material 110 are used so that the hump-forming element 102 maintains its maximum height even when the menstrual undergarment presses the absorbent article into close contact with the wearer's body. This allows the hump 100 to continuously cover a maximum amount of the inside surfaces of the wearer's labia majora and minora during use. Preferably, the hump-forming element maintains a maximum height of greater than or equal to at least one of the following amounts in use: about 10 mm, about 12 mm, about 14 mm, about 16 mm, about 18 mm, or about 20 mm.

The pieces of resilient material 110 can comprise any material that is suitable for the above purposes. The pieces of resilient material 110 may either be absorbent or non-absorbent. Suitable resilient materials include, but are not limited to absorbent and non-absorbent foams. In one version of the embodiment shown, the pieces of resilient material 110 comprise a radiation cross-linked polyethylene foam known as VOLARA, type 2A manufactured by Voltek, Inc. of Lawrence, Mass. The VOLARA foam material is three pieces. Each piece is a rectangular parallelepiped which has a square cross-section measuring about 6 mm×6 mm, and a length of about 50 mm. One piece of resilient material is positioned in each of the U-shaped portions and the inverted U-shaped portions of the first folded web.

The pieces of resilient material 110 are attached to the underside of the underlying layer 108. The pieces of resilient material 110 an be attached to the underside of the underlying layer 108 in any suitable manner, such as by adhesives or double-sided adhesive tape. The entire hump-forming element 102 is preferably secured to the absorbent core 32 in a similar manner.

In another embodiment, the absorbent article can be provided with a structure in which an absorbent element can separate (or "decouple") from the backsheet of the absorbent article. This will allow the absorbent element to move into closer contact with the wearer's body in the space between the wearer's labia while the backsheet remains in place adjacent to the menstrual undergarment.

Such an embodiment can be comprised of any suitable materials that are combined to have the capacity and flexibility described herein. In one preferred version of such an embodiment, the absorbent article comprises: a DRI-WEAVE apertured film topsheet; an underlying layer of material such as a nonwoven web, in particular a spunlaced nonwoven web such as that manufactured by E. I. DuPont Nemours & Company of Wilmington, Del., which is known as a SONTARA 8407 material (SONTARA is a registered TM of E. I. DuPont Nemours & Company); a laminate absorbent core comprising tissue and superabsorbent hydogel-forming polymeric material which is provided with the high capacity described herein; a layer comprising a patch of PUFFS facial tissue marketed by The Procter & Gamble Company of Cincinnati, Ohio; and, a backsheet comprising a stretchable laminate. While the stretchable laminate backsheet may be quite flexible, the remainder of the absorbent article will typically have to be modified as described herein to provide it with the desired flexibility.

The absorbent article may be provided with the ability to decouple if its components are provided with the features like those described in U.S. Pat. No. 5,007,906, issued to Osborn, et al. on Apr. 16, 1991 and U.S. Pat. No. 5,324,278 entitled "Sanitary Napkin Having Components Capable of Separation in Use", issued to Visscher, et al. in Jun. 28, 1994. The absorbent article may also be provided with structural features that allow a central portion thereof to assume a convex upward configuration. Such features are described in U.S. Pat. Nos. 5,171,302 and 5,197,959 issued to Buell on Dec. 15, 1992 and Mar. 30, 1993, respectively.

Figure 24:
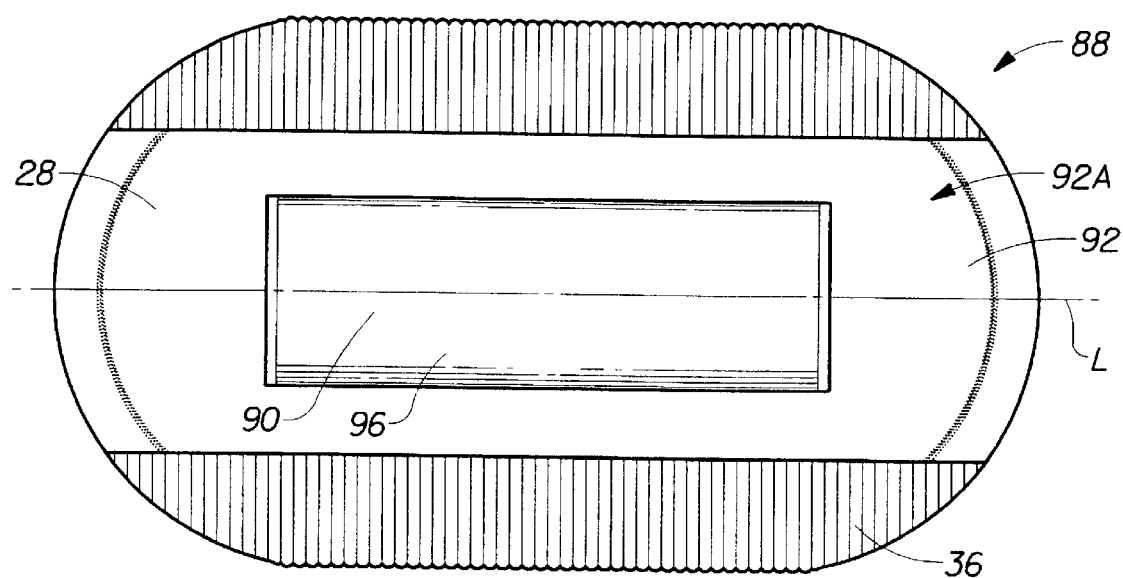
FIG. 24 is a top plan view of an alternative embodiment of the absorbent article of the present invention in the form of a compound absorbent article that has a tube of absorbent material on its body-facing side.

Still other non-limiting embodiments of the present invention are possible. For example, FIG. 24 shows a "compound" absorbent article 88 having the features of the present invention. The compound absorbent article 88 comprises a tube of absorbent material, primary absorbent component (or "core tube") 90 which is joined to the body-facing side 92A of a secondary absorbent component (or "base pad") 92.

The primary absorbent component 90 is preferably intended to absorb the bulk of bodily fluids discharged by the user. In the embodiment shown in FIG. 24, the primary absorbent component 90 comprises an absorbent structure, such as a tube of absorbent material, and an outer cover 96 that wraps the absorbent material. The outer cover 96 can comprise any of the materials described above as being suitable for the topsheet of the embodiments shown in FIGS. 1–4. In one preferred version of the embodiment shown in FIG. 24, the outer cover 96 of the primary absorbent component 90 comprises the same material used for the topsheet 28 of the base pad 92. The absorbent material can comprise any of the materials described as being suitable for use in the absorbent core of the embodiments described herein. The primary absorbent component 90 may further comprise an optional acquisition layer. The acquisition layer may be a separate component positioned between the outer cover 96 and the absorbent material, or it may be an integral part of a composite outer cover. The acquisition layer may serve several functions including improving the wicking of exudates over and into the absorbent material and/or containing material in the primary absorbent component 90.

The base pad 92 primarily functions to protect the user's garments from soiling by absorbed fluids which may be expelled from the primary absorbent component 90 or which inadvertently bypass the primary absorbent component 90. The base pad 92 of the compound absorbent article 88 shown in FIG. 24 preferably comprises the absorbent article 20 shown in FIG. 4.

The compound absorbent article shown in FIG. 24 is a less preferred embodiment for use with a menstrual undergarment such as that shown in FIGS. 7 and 8 which has an extensible lifting strip 42 along its longitudinal centerline. The lifting strip 42 places the absorbent article in close contact with the wearer's body in the space between the wearer's labia without providing a tube of absorbent material on the body-facing surface of the absorbent article.

Figure 25:
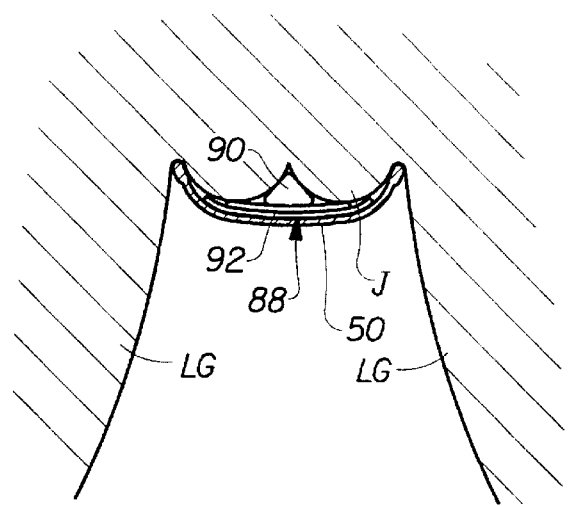
FIG. 25 is a cross-sectional view taken transversely through a portion of a wearer's body which shows how the absorbent tube of the compound absorbent article in FIG. 24 might be used to fill any gapping that may occur if an alternative menstrual undergarment is selected that has a wider lifting zone that spans the distal surfaces of the wearer's labia.

However, as shown in FIG. 25, the menstrual undergarment may be provided with a wider lifting zone that spans the distal surfaces of the wearer's labia. This wider zone may not rise convexly upward to enter the space between the wearer's labia. In such a case, the tube of absorbent material 90 on the compound absorbent article 88 will preferably work in conjunction with the menstrual undergarment as shown in FIG. 25, to provide the desired interlabial fit.

The absorbent article of the present invention can be provided with still other features. For example, the absorbent article can be provided with an optional pair of flaps that are joined to and extend laterally outward from the longitudinal side edges of the absorbent article. In this case, the absorbent article without the flaps can be considered to comprise the main body portion of the overall absorbent article which has the optional flaps. The flaps preferably extend laterally outward from at least a central region along the length of the main body portion. However, since the main body portion may be relatively small in size, it is possible that the flaps may extend outward along the entire length of the main body portion. In other embodiments, the flaps may even be longer than the main body portion.

If optional flaps are provided, they can be joined to the main body portion of the absorbent article in any suitable manner. The flaps can be integral with the main body portion (that is, the flaps can comprise integral extensions of the topsheet and backsheet). In other embodiments, the flaps can comprise separate components that are joined to the main body portion of the absorbent article.

The flaps can be in any suitable configuration. Suitable flaps are described in Reexamined Patent No. B1 4,589,876 entitled "Sanitary Napkin", issued to Van Tilburg, Certificate of Reexamination issued Apr. 27, 1993; U.S. Pat. No. 4,687,478 entitled "Shaped Sanitary Napkin With Flaps", which issued to Van Tilburg on Aug. 18, 1987; U.S. Pat. No. 5,389,094 entitled "Absorbent Article Having Flaps and Zones of Differential Extensibility" issued to Lavash, et al. on Feb. 14, 1995; U.S. Pat. No. 5,558,663 entitled "Absorbent Article Having Undergarment Covering Components With Zones of Extensibility" issued to Weinberger, et al. on Sep. 24, 1996 and U.S. Pat. No. 5,584,829 entitled "Absorbent Articles Having Panty Covering Components That Naturally Wrap the Sides of Panties", issued to Lavash, et al. on Dec. 17, 1996 (which describe alternatives to flaps that are applied by a wearer); PCT Publication No. WO 97/12576 entitled "Absorbent Article Having Flaps With a Deformed Hinge and Zones of Extensibility", published Apr. 10, 1997; and in International Patent Application Ser. No. PCT US 96/15957 entitled "Absorbent Article Having Flaps With Step Configuration and Zones of Extensibility" filed on Oct. 3, 1996, in the name of Lash, et al.

In still other embodiments, an absorbent interlabial device can be worn with the absorbent article of the present invention and the menstrual undergarment described herein. Suitable interlabial devices are described in U.S. Pat. No. 5,762,644 entitled "Toilet-Disposable Absorbent Interlabial Device", issued to Osborn, et al. on Jun. 9, 1998 and in U.S. patent application Ser. No. 09/071,425 entitled "Absorbent Interlabial Device" filed in the names of Brown, et al. on May 1, 1998. Alternatively, such an absorbent interlabial device can be worn in such a menstrual undergarment without the absorbent article of the present invention.

2. Method of Making the Absorbent Article Shown in FIGS. 18–20

The absorbent article of the present invention can be made in any suitable manner. Suitable methods for making the embodiments shown in FIGS. 1–4 and FIGS. 22–24 were described above. Since the method of making the embodiment of the absorbent article shown in FIGS. 18–20 differs, it will be described separately. A preferred embodiment of a method of making the embodiment of the absorbent article 20 shown in FIGS. 18–20 is described in greater detail below.

The absorbent article 20 shown in FIGS. 18–20 comprises an absorbent core that is preferably in the form of a plurality of particles or columns of absorbent foam material. In a preferred embodiment, the absorbent foam material is formed into particles or columns of foam when it is positioned between the topsheet 28 and the backsheet 30 to provide a self-contained web of particulate or columnar material for the absorbent core 32. Such an embodiment can be readily constructed as described herein since the absorbent foam material is more easily destructible than the topsheet or backsheet materials. In the preferred embodiment of the method of making the absorbent article shown in FIGS. 18–20, the method of forming the absorbent foam material into particulate or columnar material involves a mechanical straining process. For convenience, the following description will only refer to the process as forming particulate material (rather than both particulate and columnar material).

Figure 26:
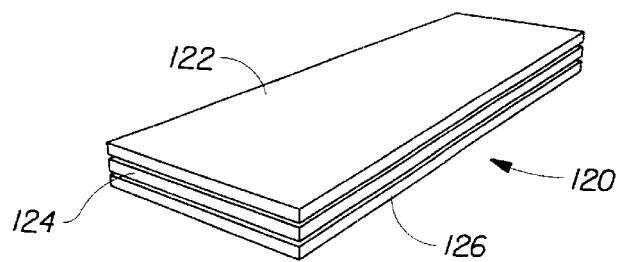
FIG. 26 is a perspective view of a composite web comprising materials for the topsheet, backsheet, and absorbent core of the absorbent article shown in FIGS. 18–20.
Figure 27:
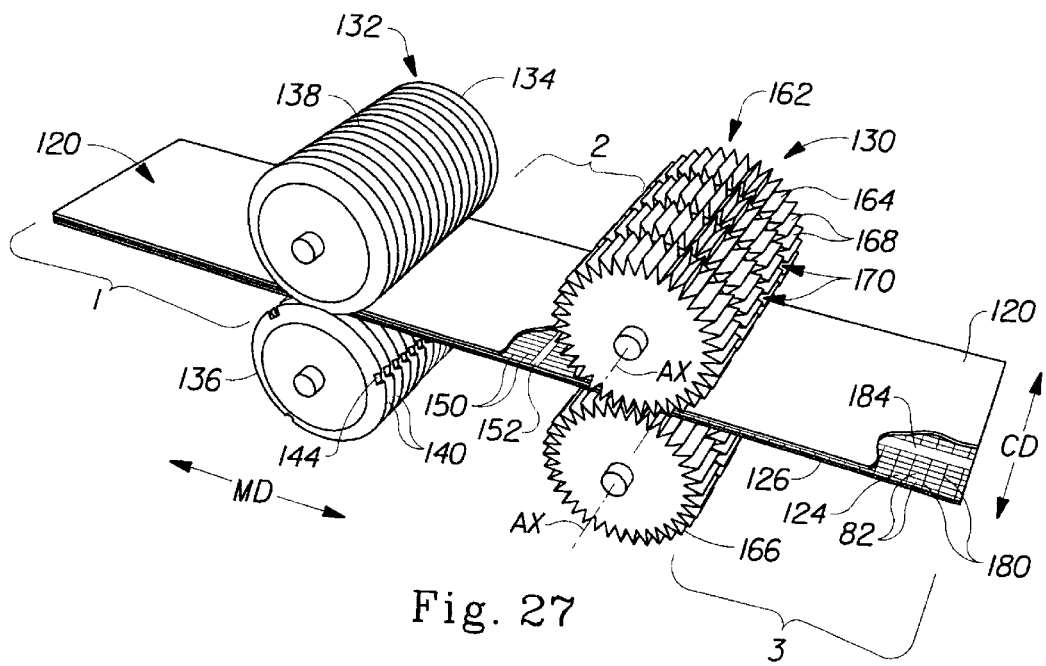
FIG. 27 is a perspective view of an apparatus used to form the absorbent material in the composite web shown in FIG. 26 into particulate material.
Figure 28:
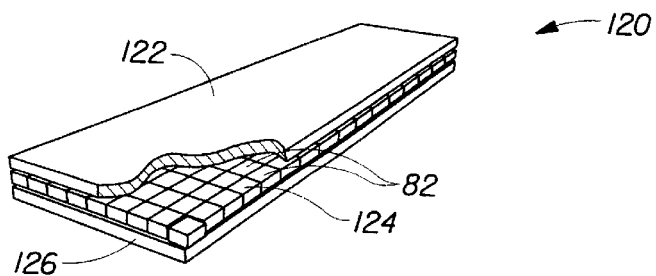
FIG. 28 is a partially fragmented perspective view of the composite web shown in FIG. 26 after it has been fed through the apparatus shown in FIG. 27.

The process of forming the absorbent foam material into particulate material comprises several steps. One non-limiting, but preferred embodiment of this process is shown in FIGS. 26–28. FIG. 26 shows that a first step in this process involves forming a composite web 120. The composite web 120 comprises from top to bottom: a web of topsheet material 122, a web of absorbent foam material 124, and a web of backsheet material 126. The web of topsheet material 122 and the web of backsheet material 126 act as "carrier webs" for the web of absorbent foam material 124 to contain the same when it is formed into particulate material.

The web of topsheet material 122 and the web of backsheet material 126 can be comprised of any of the materials specified above as being suitable for use as those components, provided that such materials have a yield to break point under tensile forces that is greater than that of the web of absorbent foam material 124. The absorbent foam material 124 has a yield to break point under tensile forces that is lower than the yield to break points of the web of topsheet material 122 and web of backsheet material 126.

In order to make the preferred embodiment shown in FIGS. 18–20, the web of topsheet material 122 will comprise a web of the high loft material described above. The web of absorbent foam material comprises one of those absorbent foam materials specified above in conjunction with the description of the embodiment shown in FIGS. 18–20. Preferably, the web of absorbent foam material 124 is about 2 mm thick. The web of backsheet material 126 preferably comprises a polyethylene film. The webs of topsheet material 122, absorbent foam material 124, and backsheet material 126 can be joined together in any manner specified above for forming the embodiment shown in FIGS. 1–3.

An apparatus for mechanically straining the composite web 120 is provided. The apparatus preferably comprises a mechanical device that has at least one component with a patterned surface thereon. The composite web 120 is then preferably subjected to a mechanical straining process using the apparatus by impressing a patterned surface into the composite web 120 so that the absorbent foam material 124 is at least partially formed into particulate material without cutting or forming the web of topsheet material 122 and the web of backsheet material 126 into particulate material.

FIG. 27 shows one embodiment of an apparatus 130 that is used to form the absorbent material 124 in the composite web 120 into particulate material. The apparatus 130 shown in FIG. 27 comprises two pairs of cylindrical rolls, first pair of rolls 132 and second pair of rolls 162. Each of the rolls has a patterned surface thereon. The patterns are preferably formed by a plurality of ridges and valleys on the rolls that define a plurality of triangularly shaped teeth.

The rolls in the first pair of rolls 132 preferably have triangularly-shaped teeth that are formed by ridges and valleys that are oriented around the circumference of the rolls. The top roll 134 and the bottom roll 136 in the first pair of rolls 132 are aligned so that the ridges 138 of the top roll 134 align with the valleys 140 on the bottom roll 136. In a preferred embodiment, the triangulari-shaped teeth that form the ridges on the top roll 134 and the valleys on the bottom roll are spaced so that these teeth do not touch each other or fully "engage". The degree to which the teeth on the opposing rolls partially intermesh is referred to herein as the "engagement" of the teeth. The engagement is the distance between a position where the apexes of the teeth on the respective rolls are in the same plane (0% engagement) to a position where the apexes of the teeth of one roll extend inward beyond the plane toward the valleys on the opposing roll. The engagement of the teeth can be expressed as a percentage of the pitch (distance between the apexes of the teeth on one of the rolls), or in terms of a measured distance. Since the height of the teeth may be greater than the pitch, the engagement may be a value that is greater than 100% (for instance, if the engagement is greater than the pitch). Preferably, the engagement is between about 15% and about 120% of the pitch length, and more preferably is about 100% of the pitch length. Examples of engagement expressed in terms of a measured distance may be between about 0.01 inch to about 0.07 inch (about 0.25 mm to about 1.8 mm), and between about 0.04 inch to about 0.06 inch (about 1 mm to about 1.5 mm).

As shown in FIG. 27, at the stage designated 1, the composite web 120 is fed in a machine direction (MD) into the nip between the rolls 134 and 136. The rolls 134 and 136 subject the composite web 120 to a mechanical straining process by impressing the patterned surfaces thereon into the composite web 120. The mechanical straining process applies a force that is greater than the yield to break point of the web of absorbent foam material 124, but less than the yield to break point of the web of topsheet material 122 and web of backsheet material 126 so that the web of absorbent foam material 124 is at least partially slit without slitting the web of topsheet material 122 and web of backsheet material 126.

FIG. 27 shows the condition of the composite web at stage 2, after it passes through the nip between the first pair of rolls 132. As shown in FIG. 27, the web of topsheet material 122 and web of backsheet material 126 will have a pattern formed therein that corresponds to the combination of the patterns on the adjacent rolls, 134 and 136 in the first pair of rolls 132. The web of topsheet material 122 and web of backsheet material 126, however, are not slit or cut. The intermediate web of absorbent foam material 124 has a plurality of slits 150 formed therein. The slits 150 are oriented in the machine direction (or "MD"). In the particular embodiment shown, the slits are intermittent and separated by cross-machine direction (or "CD") bands of unslit material 152. This is due to the presence of the optional channels 144 on the bottom roll 136. The web of absorbent foam material 124 is slit while the web of topsheet material 122 and web of backsheet material 126 are not slit because the web of absorbent foam material 124 has a lower yield to break point than the web of topsheet material 122 and web of backsheet material 126, and breaks, under tensile forces (the straining process) while the web of topsheet material 122 and web of backsheet material 126 do not.

The composite web 120 is then fed into a nip between the second set of rolls 162 of the apparatus 130 for mechanically straining the composite web. The second set of rolls 162 also comprises top and bottom rolls, 164 and 166, respectively. Each of these rolls also has a pattern on its surface. As shown in FIG. 27, the rolls 164 and 166 in the second set of rolls 162 have ridges and valleys that run parallel to the axes, AX, of these rolls. The ridges and valleys on these rolls also define triangular-shaped teeth 168. The teeth on the second pair of rolls 162 engage in a manner similar to the teeth on the first pair of rolls 132. The top roll 164 may also have several optional spaced apart channels 170 that are oriented around the circumference of the cylindrical roll. Suitable patterned rolls for use as the second pair of rolls 162 in the apparatus shown in FIG. 27 (though not for this purpose) are described in greater detail in U.S. Pat. No. 5,518,801 entitled "Web Materials Exhibiting Elastic-Like Behavior" issued to Chappell, et al. on May 21, 1996.

FIG. 27 shows that when the composite web 120 leaves the nip between the second set of rolls 162, at least a portion of the absorbent foam material 124 is further provided with a plurality of slits 180 that are oriented in the cross-machine direction (CD). This initial slitting in the machine direction and subsequent slitting in the cross machine direction causes the absorbent material 124 to be formed or chopped into a plurality of particles 82. In the preferred embodiment shown in the drawings, the particles 82 have a square surface area that is about 1.5 mm×1.5 mm. The particles 82 are preferably about 2 mm thick (the thickness of the web of absorbent foam material). The absorbent material 124 can optionally have unslit strips 184 left therein due to the presence of the channels 170 in the second pair of rolls 162.

Again, the web of topsheet material 122 and web of backsheet material 126 are not slit, but have another pattern formed therein. The overall pattern formed therein resembles a grid with a combination of the impressions created by the first and second sets of rolls 132 and 162.

FIG. 28 shows the composite web 120 after it has been fed through the apparatus shown in FIG. 27. It should be understood that in FIG. 28, the pattern impressed into the web of topsheet material 122 and web of backsheet material 126 by the first and second sets of rolls has been omitted for simplicity. In addition, the absorbent foam material 124 is shown as comprising only particles 82 for simplicity (that is, no unslit strips are shown as being left in the absorbent foam material 124). Such an embodiment could be created by providing the rolls in the first and second sets of rolls 132 and 162 with continuous teeth and omitting the channels 144 and 170 between the teeth.

Methods of forming a web of material into particulate material are described in greater detail in U.S. patent application Ser. Nos. 09/027,039 and 09/027,379 entitled "Method of Making a Slitted or Particulate Absorbent Material and Structures Formed Thereby" and "Method of Making a Slitted or Particulate Absorbent Material" filed in the name of McFall, et al. on Feb. 20, 1998.

The composite web 120 with particles of absorbent foam material 82 inside can then be cut into individual absorbent articles in the shape shown in FIGS. 18–20. If desired, the components of the cut absorbent articles, such as the topsheet and backsheet, may be at least partially peripherally joined, and the fastening material can be added to the garment-facing side of the absorbent articles.

3. Test Methods

A. Flexure-resistance

The flexure-resistance of an absorbent article is measured by peak bending stiffness. Peak bending stiffness is determined by a test which is modeled after the ASTM D 4032.82 Circular Bend Procedure, the procedure being considerably modified and performed as follows: The Circular Bend Procedure is a simultaneous multi-directional deformation of a material in which one face of a specimen becomes concave and the other face becomes convex. The Circular Bend Procedure gives a force value related to flexure-resistance, simultaneously averaging stiffness in all directions.

Apparatus

The apparatus necessary for the Circular Bend Procedure is a modified Circular Bend Stiffness Tester, having the following parts:

A smooth-polished steel plate platform which is 102.0× 102.0×6.35 millimeters having an 18.75 millimeter diameter orifice. The lap edge of the orifice should be at a 45 degree angle to a depth of 4.75 millimeters.

A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to be the exact bottom of the plate orifice.

A force-measurement gauge and more specifically an Instron inverted compression load cell. The load cell has a load range of from about 0.0 to about 2000.0 grams.

An actuator, and more specifically the Instron Model No. 1122 having an inverted compression load cell. The Instron 1122 is made by the Instron Engineering Corporation, Canton, Mass.

Number and Preparation of Specimens

In order to perform the procedure for this test, as explained below, five representative absorbent articles are necessary. From one of the five articles (having, of course, any panty adhesive release paper removed and any adhesive blocked) to be tested, some number "Y" of 37.5×37.5 millimeter test specimens are cut. Specimens having portions in which a topsheet is joined directly to a barrier sheet or which are a laminate of a topsheet, two or less tissue sheets and a barrier sheet, should not be tested. The reason that these specimens are not tested is due to the realization that prior art absorbent articles exist in which a topsheet is joined to a barrier sheet beyond the edges of an absorbent core in the periphery of the napkin, such portions of which are highly flexible. However, the present invention is more concerned with the overall flexibility of the absorbent article and not merely the peripheral portions thereof and, therefore, the flexibility of the present invention is more concerned with the flexibility of the significant absorbent portions of the absorbent article. If any of these significant absorbent portions of the absorbent article meet the parameters of this test, then the absorbent article satisfies the test. Therefore, a number of different specimens should be tested from each absorbent article. Certainly, the structurally most flexible portion of the absorbent article should be tested, excluding those portions excluded above. The test specimens should not be folded or bent by the test person, and the handling of specimens must be kept to a minimum and to the edges to avoid affecting flexural-resistance properties. From the four remaining absorbent articles, an equal number "Y" of 37.5×37.5 millimeter specimens, identical to the specimens cut from the first absorbent article, are cut. Thus, the test person should have "Y" number of sets of five identical specimens.

The procedure for the Circular Bend Procedure is as follows. The specimens are conditioned by leaving them in a room which is 21±1° C. and 50±2% relative humidity for a period of two hours. The tests described herein are conducted under similar conditions. The test plate is leveled. The plunger speed is set at 50.0 centimeters per minute per full stroke length. A specimen is centered on the orifice below the plunger such that the body surface of the specimen is facing the plunger and the garment surface of the specimen is facing the platform. Of course, any panty adhesive release paper (if present) is removed, to simulate in-use conditions. Any panty adhesive (if present) should be blocked, using means well known to those skilled in the art, such as glycerin and/or powder, to prevent the specimen from adhering to the platform and an artificially high peak bending stiffness being obtained. If desired, the specimen may be centered over the orifice with the body surface facing the platform and the garment surface facing the plunger to obviate the need for blocking any adhesive which may be present. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

Calculations

The peak bending stiffness for each specimen is the maximum force reading for that specimen. Each set of five identical specimens is tested and the five values received for that set are averaged. Thus, the test person now has an average value for each of the "Y" sets tested. The flexure-resistance for an absorbent article is the greatest flexibility of these average peak bending stiffnesses.

B. Capacity

The total capacity of an absorbent article is determined as follows. Any panty adhesive release paper is removed from the article to be tested. The article is weighed to the nearest 0.1 gram. The article is then submerged in a beaker of sterile saline (obtainable from the Baxter Travenol Company of Deerfield, Ill.), such that the article is totally submerged and is not bent or otherwise twisted or folded. The article is submerged for 10 minutes. The article is removed from the saline and suspended for two minutes in a vertical position to allow the saline to drain out of the article. The article is then placed body facing surface down onto an absorbent blotter, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotter is replaced every 30 seconds until the amount of fluid transferred to the absorbent blotter is less than 0.5 grams in a 30 second period. Next, the article is weighed to the nearest 0.1 gram and the dry weight of the article is subtracted. The difference in grams is the total capacity of the article. This concludes the test.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

It should also be understood that all of the limits and ranges specified herein include all narrower ranges, limits, and amounts that are within the specified limits and ranges and that such narrower ranges and limits may be claimed even though those limits and ranges are not separately listed.

While particular embodiments of the present invention have been illustrated and described, it would be obvious to those skilled in the art that various other changes and modifications can be made without departing from the spirit and scope of the invention.

What is claimed is:

1. An absorbent article for wearing in a supporting garment, said absorbent article comprising:
    a liquid pervious side;
    a liquid impervious side opposite said liquid pervious side; and
    an absorbent component between said liquid pervious side and said liquid impervious side, wherein said liquid pervious side and said liquid impervious side are arranged to form a unitary structure wherein said liquid pervious side comprises a liquid pervious topsheet comprising a fibrous nonwoven web having a maximum caliper measured under a pressure of 0.005 psi of greater than or equal to ⅛ inch (3.2 mm), and a basis weight of less than or equal to 5 oz./yd$^2$ (142 g/m);
    wherein said absorbent article is characterized in that it has a flexure resistance of less than or equal to 100 grams and is capable of substantially maintaining sustained contact with and covering at least a portion of the inside surfaces of the wearer's labia, at least a portion of the exterior surfaces of the wearer's labia, and at least a portion of the supporting garment.

2. The absorbent article of claim 1 which has a longitudinal central region that is capable of being positioned in the space between the wearer's labia, said longitudinal central region being capable of residing in said space between the wearer's labia at an elevation that is higher than at least some portions of the absorbent article that are located laterally outboard of said longitudinal central region.

3. An absorbent article according to claim 2 wherein said absorbent article is capable of assuming such a configuration without compression by the inner portion of a wearer's thighs.

4. An absorbent article according to claim 1 which is generally planar prior to use.

5. An absorbent article according to claim 1 which has a body-facing side with a raised portion thereon.

6. The absorbent article of claim 5 wherein said raised portion comprises a tube of absorbent material joined to said liquid pervious side of said absorbent article.

7. The absorbent article of claim 5 wherein said raised portion comprises a hump-forming element, and said liquid pervious side comprises a liquid pervious topsheet, wherein said hump-forming element underlies said liquid pervious topsheet.

8. The absorbent article of claim 2 wherein portions of said absorbent article outside said longitudinal central region are capable of cupping the wearer's labia from the front of the labia to the back of the labia.

9. An absorbent article according to any of the preceding claims which has a cup-shaped configuration prior to use.

10. An absorbent article according to claim 1 wherein the supporting garment has a crotch region in which said absorbent article is worn assumes a modified cusp-shaped configuration when worn, wherein the cusp-shaped configuration is modified in that the supporting garment assumes a rounded convex upward shape in the longitudinally-oriented area centered about the space between the wearer's labia which lies between two convex downwardly curved portions, and said absorbent article assumes a similar configuration as the crotch region of the supporting garment.

11. An absorbent article according to claim 1 at least some of the portions of said absorbent article that are capable of maintaining contact with and covering at least a portion of the inside surfaces of the wearer's labia and the exterior surfaces of the wearer's labia will flex under a pressure of less than or equal to 20 g/cm$^2$.

12. An absorbent article according to claim 1 which is of a size and configuration to only cover a female wearer's vaginal pudendal region and perineum, and does not extend forward beyond the wearer's mons pubis or rearward to the wearer's anus.

13. An absorbent article according to claim 1 which is less than or equal to 7 inches (18 cm) in length.

14. An absorbent article according to claim 1 which has a capacity of greater than or equal to 10 grams of liquid in an area measuring 2 inches in width by 5 inches in length (5 cm by 13 cm) that will be centered under the vaginal orifice when the absorbent article is worn.

15. An absorbent article according to claim 14 having a capacity in said area of greater than or equal to 20 grams of liquid.

16. An absorbent article according to claim 1 which is capable of covering substantially all of the interior surfaces of the wearer's labia up to and including the floor of the wearer's vestibule.

17. An absorbent article according to claim 1 which is capable of covering substantially all of the exterior surfaces of the wearer's labia.

18. An absorbent article according to claim 1 which has a surface area of less than or equal to 20 in$^2$ (130 cm$^2$).

19. An absorbent article according to claim 1 which has a ratio of total capacity to surface area of greater than or equal to 2 g/in$^2$ (0.3 g/cm$^2$).

20. An absorbent article according to claim 1 having a flexure resistance of between 20 and 75 grams.

21. An absorbent article according to claim 1 wherein said absorbent article is of a size and configuration that is resistant to being contacted by the insides of the upper portions of a wearer's thighs and does not shift more than 1.5 inch (3.8 cm) from its position relative to the wearer's vaginal introitus when the absorbent article is worn in a supporting garment.

22. An absorbent article according to claim 1 wherein the liquid pervious side of said absorbent article comprises a plurality of elements extending outward from the body-contacting surface of said liquid pervious side.

23. The absorbent article of claim 22 wherein said elements are capable of penetrating the wearer's pubic hairs.

24. The absorbent article of claims 22 or 23 wherein said elements comprise fibers.

25. The absorbent article of claim 22 wherein said liquid pervious side comprises an apertured nonwoven web, which is generally planar, said apertured nonwoven web having apertures and unapertured portions, and said elements comprise a plurality of fibrils on said unapertured portions of said nonwoven web that extend outward from the plane of said nonwoven web.

26. The absorbent article of claim 2 wherein said topsheet has a maximum caliper of between ¼ inch (6.4 mm) and ½ inch (13 mm).

27. An absorbent article according to claim 1 further comprising a mechanical fastening material on said garment-facing surface for engaging at least a portion of the supporting garment, said mechanical fastening material comprising an array of prongs, each of said prongs comprising a base joined to a substrate, an engaging means, and a shank comprising a proximal end joined to said base and a distal end joined to said engaging means.

28. The absorbent article of claim 27 wherein said mechanical fastening material is arranged in a pattern on said garment-facing side that corresponds with a preselected portion of said supporting garment.

* * * * *